US010803146B2

(12) United States Patent
Cosse

(10) Patent No.: US 10,803,146 B2
(45) Date of Patent: Oct. 13, 2020

(54) SYSTEMS AND METHODS FOR COMMUNICATING ORTHODONTIC TREATMENT INFORMATION

(71) Applicant: Iamthinking LLC, Shreveport, LA (US)

(72) Inventor: Christopher C. Cosse, Shreveport, LA (US)

(73) Assignee: Iamthinking LLC, Shreveport, LA (US)

( * ) Notice: Subject to any disclaimer, the term of this patent is extended or adjusted under 35 U.S.C. 154(b) by 684 days.

(21) Appl. No.: 15/152,320

(22) Filed: May 11, 2016

(65) Prior Publication Data

US 2016/0335408 A1 Nov. 17, 2016

Related U.S. Application Data

(60) Provisional application No. 62/160,457, filed on May 12, 2015.

(51) Int. Cl.
*G06F 19/00* (2018.01)

(52) U.S. Cl.
CPC ................. *G06F 19/3418* (2013.01)

(58) Field of Classification Search
None
See application file for complete search history.

(56) References Cited

U.S. PATENT DOCUMENTS

| 2006/0031094 | A1* | 2/2006 | Cohen | G06F 19/328 |
| | | | | 705/2 |
| 2008/0109253 | A1* | 5/2008 | D'Ambrosio | G06Q 50/22 |
| | | | | 705/2 |
| 2008/0262866 | A1* | 10/2008 | Greene | G06Q 50/22 |
| | | | | 705/2 |
| 2008/0306724 | A1* | 12/2008 | Kitching | G16H 50/50 |
| | | | | 704/2 |
| 2011/0208537 | A1* | 8/2011 | Sachdeva | G06Q 50/22 |
| | | | | 705/2 |
| 2013/0185348 | A1* | 7/2013 | Hall | G06Q 10/0633 |
| | | | | 709/203 |
| 2014/0081988 | A1* | 3/2014 | Woods | G06Q 10/101 |
| | | | | 707/748 |
| 2014/0122027 | A1* | 5/2014 | Andreiko | A61C 7/002 |
| | | | | 703/1 |
| 2014/0204190 | A1* | 7/2014 | Rosenblatt, III | H04N 7/14 |
| | | | | 348/77 |

(Continued)

*Primary Examiner* — Michael Tomaszewski
*Assistant Examiner* — Jay M. Patel
(74) *Attorney, Agent, or Firm* — DASCENZO Intellectual Property Law, P.C.

(57) ABSTRACT

Systems and methods for communicating orthodontic treatment information are disclosed herein. The methods may include methods of delivering an informational resource corresponding to an orthodontic treatment instruction to a patient of an orthodontist, and optionally to a caretaker of the patient and a dentist of the patient. The methods may further include delivering receipt information to the orthodontist and/or the caretaker, wherein the receipt information is indicative of an interaction between the patient and the informational resource. The systems may include electronic devices and interfaces associated with the orthodontist, the patient, the caretaker, and the dentist that may facilitate the communication methods.

24 Claims, 7 Drawing Sheets

(56) References Cited

U.S. PATENT DOCUMENTS

| | | | |
|---|---|---|---|
| 2014/0379356 A1* | 12/2014 | Sachdeva | A61C 7/002 |
| | | | 705/2 |
| 2015/0019252 A1* | 1/2015 | Dawson | G06F 19/3481 |
| | | | 705/3 |
| 2015/0025907 A1* | 1/2015 | Trosien | G06Q 10/10 |
| | | | 705/2 |
| 2015/0112702 A1* | 4/2015 | Joao | G16H 10/60 |
| | | | 705/2 |
| 2015/0332017 A1* | 11/2015 | Swanson | G06F 19/3456 |
| | | | 705/3 |
| 2015/0363573 A1* | 12/2015 | Schneider | G06F 19/3468 |
| | | | 705/2 |
| 2016/0124920 A1* | 5/2016 | Golay | G06F 17/2247 |
| | | | 705/3 |
| 2017/0296303 A1* | 10/2017 | Tod | A61C 7/002 |

\* cited by examiner

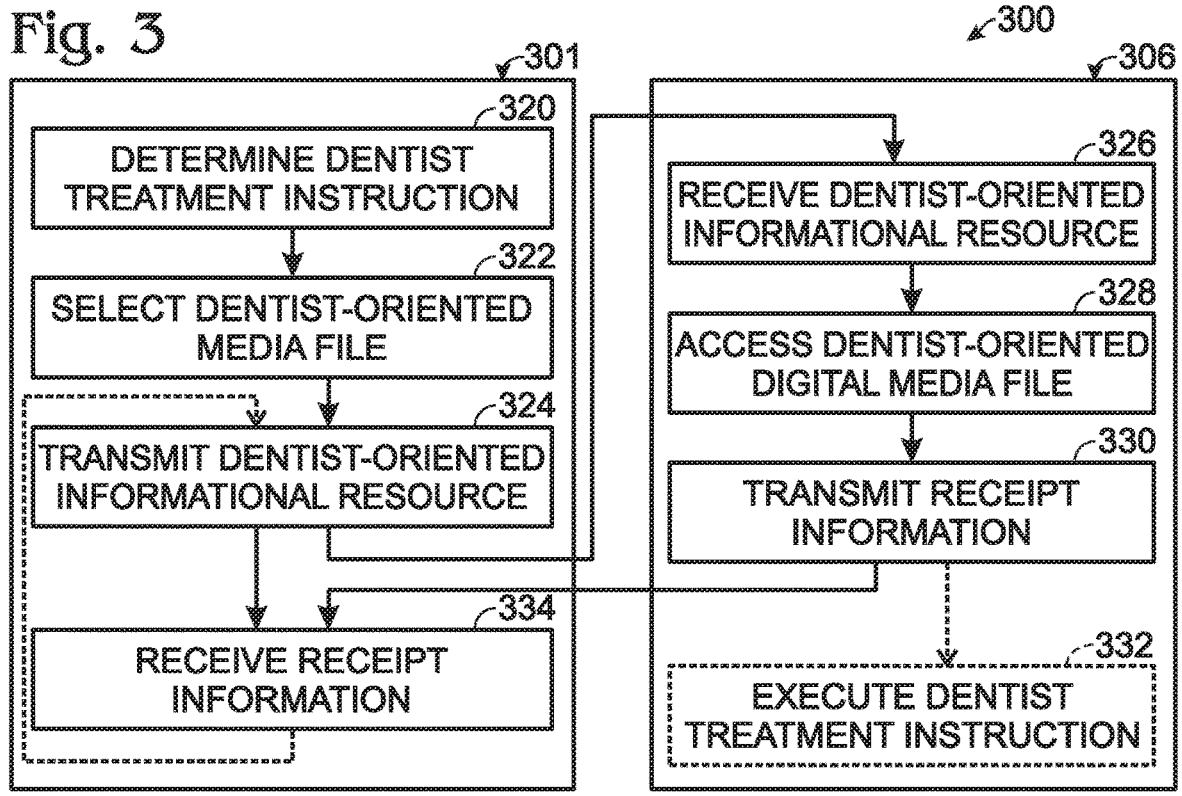
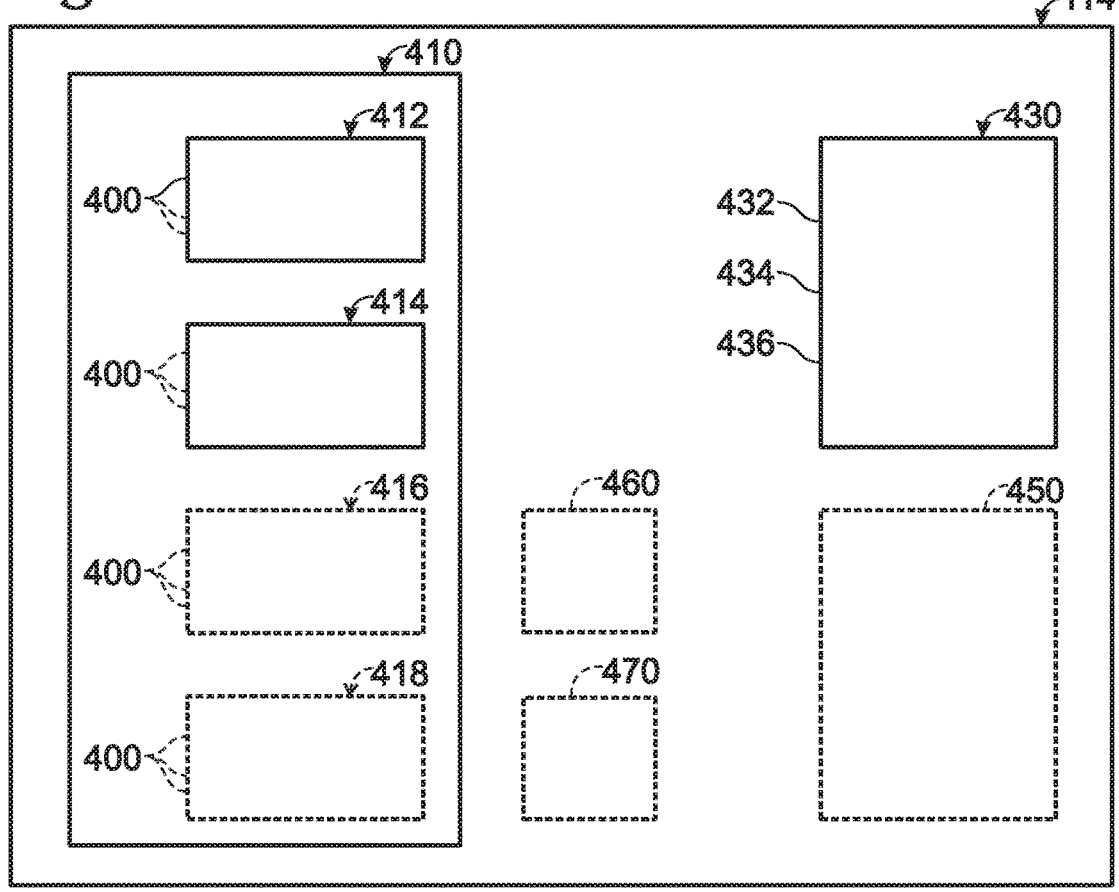

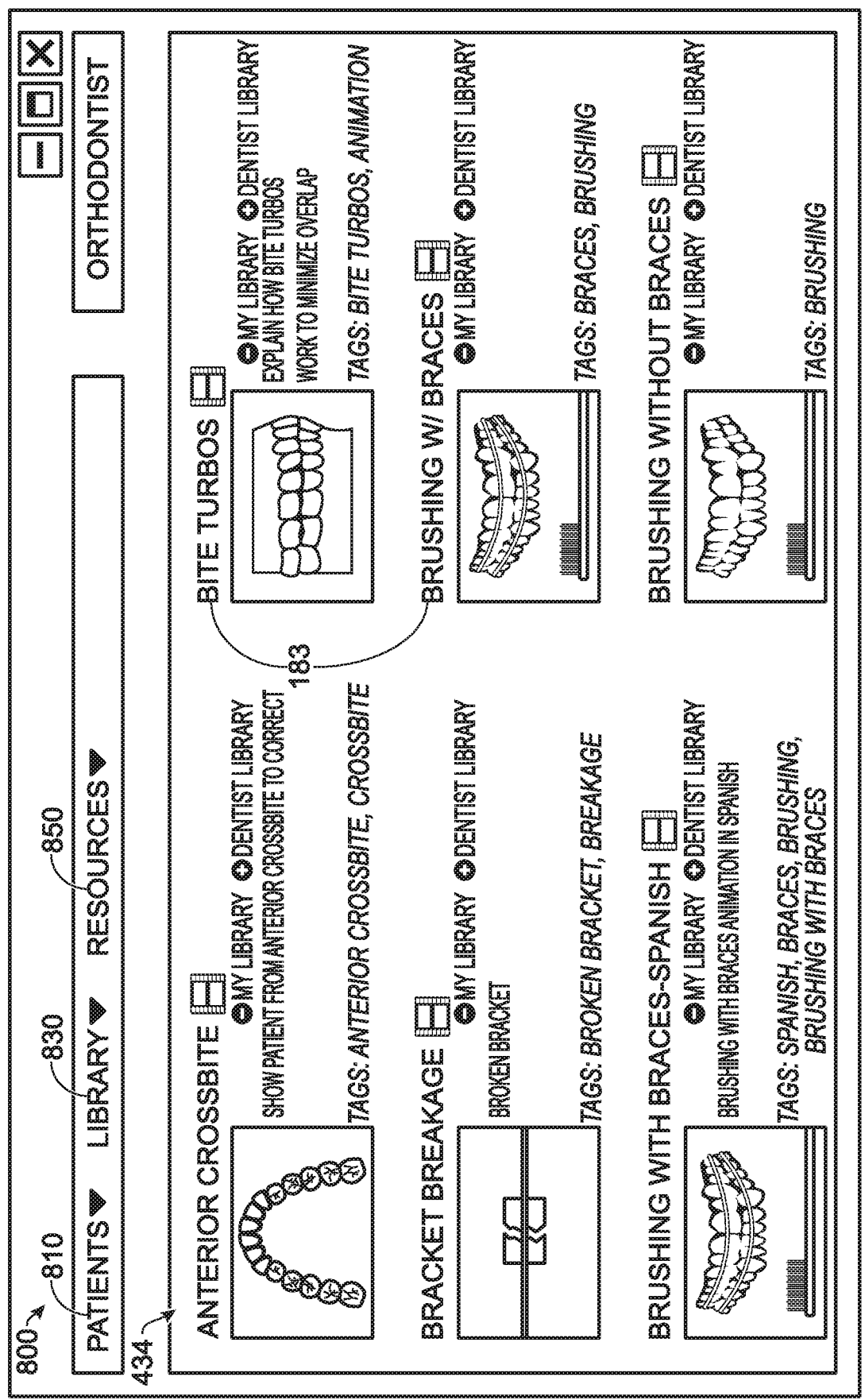

SYSTEMS AND METHODS FOR COMMUNICATING ORTHODONTIC TREATMENT INFORMATION

RELATED APPLICATION

This application claims priority under 35 U.S.C. §119(e) to U.S. Provisional Patent Application Ser. No. 62/160,457, which was filed on May 12, 2015, and the complete disclosure of which is hereby incorporated by reference.

FIELD OF THE DISCLOSURE

The present disclosure relates generally to coordinating information transfer in the orthodontics and dental fields, and more particularly to coordinating information transfer between at least an orthodontist and a patient.

BACKGROUND OF THE DISCLOSURE

During the course of an orthodontic treatment plan, which may span several years, the effectiveness and efficiency of the treatment generally depends on the services provided by an orthodontist and the patient's compliance with the orthodontist's home care instructions. For instance, while an orthodontist may routinely alter the prescriptive forces imparted on the patient's teeth by the orthodontic treatment, a patient may be responsible for maintaining the orthodontic braces and teeth in a sufficiently clean and undamaged state. Additionally, a patient may be responsible for utilizing and maintaining orthodontic accessories, such as rubber bands, head gear, removable dental aligners, and retainers. If a patient fails to adequately receive and/or follow an orthodontist's home care instructions, the orthodontic treatment plan may be delayed and/or the braces may need to be replaced, leading to additional inconvenience and frustration for the orthodontist, the patient, and/or the patient's parents or guardians. A patient's failure to adequately comply with an orthodontist's home care instructions may result from an instruction that is communicated in person but that is misunderstood, forgotten, or ignored, especially if the patient is a child whose parents or guardians are not present when the instruction is delivered. Thus, there exists a need for improved systems and methods for coordinating information transfer.

SUMMARY OF THE DISCLOSURE

Systems and methods for communicating orthodontic treatment information are disclosed herein. The methods may include methods of providing orthodontic treatment instructions to a patient of an orthodontist, wherein the orthodontist creates or selects an informational resource corresponding to a treatment instruction and delivers the informational resource to the patient.

Responsive to an interaction between the patient and the informational resource, the orthodontist may receive receipt information that is indicative of said interaction. Responsive to the receipt information, the orthodontist may repeat the delivery of the informational resource to the patient to encourage receipt and observance of the treatment instruction. In methods according to the present disclosure, the informational resource and/or receipt information additionally or alternatively may be sent to a caretaker of the patient and/or a dentist of the patient. Responsive to the receipt information, the caretaker may take actions to encourage receipt and observance of the instruction by the patient.

The methods may further include the delivery of an informational resource corresponding to an orthodontic treatment instruction from an orthodontist of a patient to a dentist of the patient, wherein the orthodontic treatment instructions are intended to be carried out by the dentist. Responsive to an interaction between the dentist and the informational resource, the orthodontist may receive receipt information that is indicative of said interaction.

Systems according to the present disclosure may include electronic devices and graphical interfaces associated with and configured to interact with the orthodontist and at least one of the patient and the caretaker of the patient, and optionally with the dentist of the patient. The electronic devices may be configured to enable the respective parties to receive, view, and transmit information, and in particular information relating to orthodontic treatment instructions according to the present disclosure. Electronic devices, graphical interfaces, and systems for enabling such communication are disclosed herein.

BRIEF DESCRIPTIONS OF THE DRAWINGS

FIG. 3 is a flowchart schematically representing additional examples of interactions, instructions, and/or types of information that may be transferred utilizing the systems and methods according to the present disclosure.

FIG. 4 is a schematic representation of a graphical interface for an orthodontist according to the present disclosure.

FIG. 10 is an additional example of a user interface that may be utilized with systems and/or methods according to the present disclosure.

DETAILED DESCRIPTION AND BEST MODE OF THE DISCLOSURE

Figure 1:
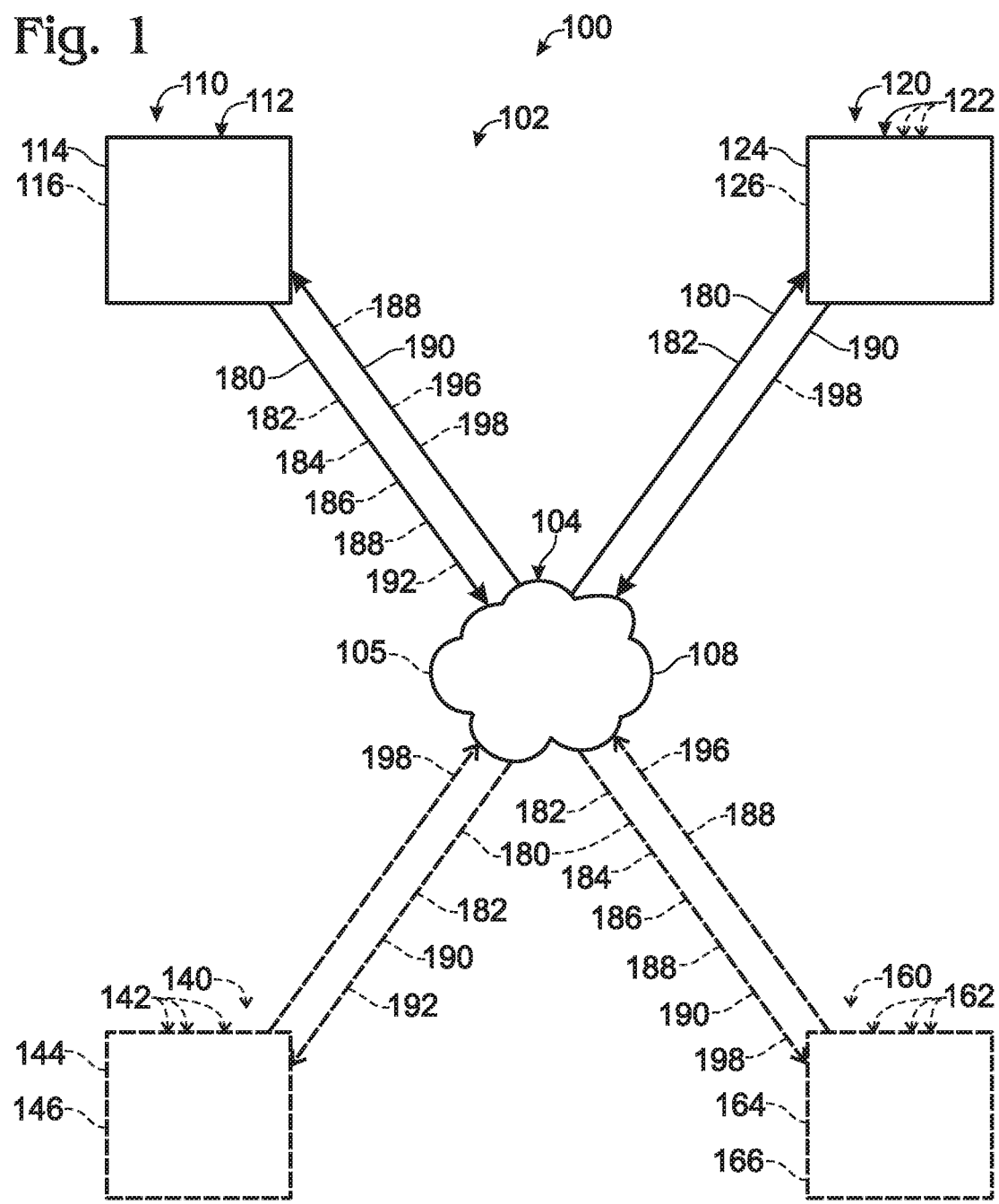
FIG. 1 is a schematic diagram representing systems, according to the present disclosure, for coordinating information transfer.

FIGS. 1-10 provide examples of computer and/or network systems 100 according to the present disclosure, of components of computer and/or network systems 100, and/or of methods 200 and 300 according to the present disclosure. Elements that serve a similar, or at least substantially similar, purpose are labeled with like numbers in each of FIGS. 1-10, and these elements may not be discussed in detail herein with reference to each of FIGS. 1-10. Similarly, all elements may not be labeled in each of FIGS. 1-10, but reference numerals associated therewith may be utilized herein for consistency. Elements, components, and/or features that are discussed herein with reference to one or more of FIGS. 1-10 may be included and/or utilized with any of FIGS. 1-10 without departing from the scope of the present disclosure.

In general, elements that are likely to be included in a given (i.e., a particular) embodiment are illustrated in solid lines, while elements that are optional to a given embodiment are illustrated in dashed lines. However, elements that are shown in solid lines are not essential to all embodiments, and an element shown in solid lines may be omitted from a given embodiment without departing from the scope of the present disclosure.

The present disclosure relates to coordinating information transfer, such as of informational resources that may be associated with instructions relating to orthodontic and/or other dental care. More specifically, disclosed herein are computer and/or network systems 100, and methods 200 and 300 that may be implemented at least in part by a system 100 according to the present disclosure. FIG. 1 schematically represents an example of systems 100, including a computer network 102 associated with a communication infrastructure 104. Communication infrastructure 104 may be or include the Internet and/or other wireless wide-area communication network for communication and/or exchange of data between two or more of an orthodontist 110, a patient 120, a caretaker 140 of patient 120, and/or a dentist 160 of patient 120. Orthodontist 110, patient 120, caretaker 140, and dentist 160 are schematically depicted in FIG. 1 to indicate their respective association with the corresponding electronic devices and intended interaction therewith, but do not form a portion of system 100 itself.

Patient 120 is an individual who is receiving medical treatment such as orthodontic or dental treatment. For example, a patient 120 of an orthodontist 110 is a patient who is receiving orthodontic treatment, such as an individual with braces or other orthodontic devices installed on the patient's teeth. Additionally or alternatively, patient 120 may refer to a designated individual acting on behalf of an individual receiving medical treatment, as previously described. For instance, if the individual receiving medical treatment is unable to directly utilize the systems and/or methods described herein, for example due to limited access to technological resources or limited autonomy, patient 120 may refer to a parent, family member, or other designated individual who may receive treatment instructions and deliver the instructions to the individual receiving medical treatment.

Examples of orthodontist 110 include a medical professional or a team of medical professionals who is/are providing orthodontic treatment and/or other orthodontic healthcare to the patient 120. As used herein, orthodontist 110 additionally or alternatively may include a group, or team, of such individuals, the staff and assistants of such individuals, etc. Thus, orthodontist 110 may include an individual orthodontist; a group, practice, or team of orthodontists; and/or the technicians, staff, and/or assistants of the orthodontist(s).

Over the course of an orthodontic treatment plan, such as a treatment plan that orthodontist 110 has designed for patient 120, it may be necessary for patient 120 to perform certain tasks prior to and/or following orthodontic office visits. Such tasks may pertain to the routine cleaning and/or maintenance of the patient's orthodontic hardware and/or teeth, and/or to the proper use of orthodontic accessories, such as rubber bands, head gear, removable dental aligners, and retainers. In order to enable and/or encourage the proper execution of such tasks, the orthodontist 110 may provide the patient 120 with instructions pertaining to such tasks remotely, i.e., without requiring that the instructions be delivered in person and/or during an orthodontic appointment. Systems and methods according to the present disclosure may further provide the orthodontist with information indicating the patient's receipt and/or access of the orthodontic instructions.

Caretaker 140 may include any suitable person, group of people, or entity that may be associated with patient 120. Examples of caretaker 140 include one or more of a parent of patient 120, a relative or other family member of patient 120, a legal guardian of patient 120, and an individual who is authorized to view the orthodontic treatment records of patient 120. Systems and methods according to the present disclosure may allow caretaker 140 to receive copies and/or indications of the instructions provided to patient 120 by orthodontist 110, and/or information indicating the patient's receipt and/or access of the orthodontic instructions. Caretaker 140 may use this information to encourage, instruct, and/or require compliance with the orthodontic instructions by patient 120, such as to avoid the cost and frustration of an unnecessarily protracted treatment plan.

Dentist 160 may include any suitable person, group of people, or entity that may be providing dental treatment and/or other dental healthcare to patient 120. Examples of dentist 160 include one or more of a general practice dentist, a dental hygienist, an oral surgeon, an endodontic specialist, a periodontist, a prosthodontist, and/or a dental technician. As used herein, dentist 160 additionally or alternatively may include a group, or team, of such individuals, the staff and assistants of such individuals, etc. It is within the scope of the present disclosure that the orthodontist 110 may provide the dentist 160 with dental care instructions, treatment recommendations, and/or comments pertaining to patient 120. For instance, the orthodontist 110 may provide the dentist 160 with specialized cleaning instructions pertaining to the orthodontic treatment and/or suggestions regarding dental procedures recommended for patient 120.

In FIG. 1, orthodontist 110, patient 120, caretaker 140, and dentist 160 may be distinct individuals or parties that may have corresponding electronic devices. For example, orthodontist 110 may have an orthodontist electronic device 112, patient 120 may have a patient electronic device 122, caretaker 140 may have a caretaker electronic device 142, and/or dentist 160 may have a dentist electronic device 162, each of which may communicate with one another, such as via communication infrastructure 104, in accordance with a method 200 and/or 300 according to the present disclosure and/or during use of a system 100 according to the present disclosure. When present in systems 100, orthodontist electronic device 112, patient electronic device 122, caretaker electronic device 142, and dentist electronic device 162, respectively, have an orthodontist graphical interface 114, a patient graphical interface 124, a caretaker graphical interface 144, and a dentist graphical interface 164, with which the corresponding user interacts with the electronic device.

Additionally, orthodontist electronic device 112, patient electronic device 122, caretaker electronic device 142, and dentist electronic device 162, respectively, may have an orthodontist local media library 116, a patient local media library 126, a caretaker local media library 146, and a orthodontist local media library 166, each of which may be configured to store and/or provide access to one or more digital media files to be accessed via the corresponding graphical interface by the corresponding user. Additionally, communication infrastructure 104 of systems 100 may include a global media library 108 configured to store and/or provide access to one or more digital media files to be accessed by one or more of orthodontist 110, patient 120, caretaker 140, and/or dentist 160 via the corresponding electronic devices. For example, global media library 108 may include one or more digital media files that may be selected by orthodontist 110 and provided to patient 120. Alternatively, orthodontist 110 may select a digital media file from orthodontist local media library 116 to be transmitted to patient electronic device 122. Patient electronic device 122 may be configured to access a digital media file that is stored external to patient electronic device 122, such as in orthodontist local media library 116 and/or global media library 108, and/or may be configured to access a copy of the digital media file stored locally in patient local media library 126.

In general, orthodontist 110 may oversee the treatment of a plurality of patients 120, each of whom may be associated with at least one caretaker 140 and at least one dentist 160. As an example, and when performing one or more steps of methods 200 and/or 300 according to the present disclosure, orthodontist 110, patient 120, caretaker 140, and/or dentist 160 may input information into and/or receive information from orthodontist electronic device 112, patient electronic device 122, caretaker electronic device 142, and/or dentist electronic device 162, such as via the user interfaces of the devices. In addition, the corresponding electronic device(s) also may display relevant information to the orthodontist, to the patient, to the caretaker, and/or to the dentist. However, this is not required to all embodiments, and it is within the scope of the present disclosure that one or more communications may be performed in an alternative manner.

Orthodontist electronic device 112, patient electronic device 122, caretaker electronic device 142, and dentist electronic device 162, when utilized, may include and/or be any suitable electronic device that may include a user interface for receiving and/or displaying information. Examples of electronic devices according to the present disclosure include servers, desktop computers, laptop computers, mobile electronic devices, tablet computers, handheld electronic devices, and/or cellular/smart phones. Such electronic devices may receive and/or display information via any suitable computer program, program code, web site, web interface, and/or mobile application.

Orthodontist electronic device 112 utilized by orthodontist 110 and/or dentist electronic device 162 utilized by dentist 160 may be different types of electronic devices than those utilized by patient 120 and caretaker 140. As an example, orthodontist electronic device 112 and/or dentist electronic device 162 may feature an increased capability and/or capacity for medical records and/or digital files to be shared as compared to patient electronic device 122 and/or caretaker electronic device 142. As further examples, orthodontist electronic device 112 and/or dentist electronic device 162 may be a part of a computer network of the orthodontist's and/or the dentist's practice, may interact with and/or otherwise have access to medical records and/or treatment devices associated with the orthodontist's and/or the dentist's practice, may include and/or have access to global media library 108 of digital media files, etc.

With continued reference to FIG. 1, systems and methods according to the present disclosure optionally additionally may include, utilize, and/or otherwise employ an information router 105. Information router 105 may be a component of and/or a system within communication infrastructure 104, and may be an automated electronic information router 105 or may be an individual controlling an associated electronic device. Information router 105 may include and/or be any appropriate software and/or hardware configured to coordinate information transfer among orthodontist 110, patient 120, caretaker 140, and/or dentist 160. For example, information router 105 may be configured to receive information from orthodontist 110 and distribute the information to the desired party or parties among patient 120, caretaker 140, and/or dentist 160, or vice versa. Information transfer that takes place through information router 105 may be referred to as indirect information transfer, whereas information transfer that takes place directly between orthodontist 110 and any other party, i.e., without utilizing information router 105 as an intermediary, may be referred to as direct information transfer. Examples of an information router 105 include a third party, service, or administrator, etc. that manage and/or enable a plurality of orthodontists and/or dentists to utilize the systems and/or methods described herein, such as to communicate orthodontic and/or dental treatment information about and/or to a plurality of patients and/or caregivers.

As a more specific example, and as discussed in more detail herein, patient 120 may receive a patient-oriented informational resource 180 via communication infrastructure 104, with the informational resource being selected and/or provided by orthodontist 110, such as responsive to a recent appointment, treatment, or other interaction between the patient and the orthodontist. As used herein, patient-oriented informational resource 180 additionally or alternatively may be referred to as a resource link 180, a resource access code 180, and/or an instructive resource 180. The patient-oriented informational resource 180 may include a patient-oriented digital media file 182, and/or a provision for accessing the patient-oriented digital media file 182. The patient-oriented digital media file 182 is configured to communicate an orthodontic and/or dental instruction to the patient. Examples of patient-oriented informational resource 180 include a link to a web site (or other wireless file server or file transfer protocol) for accessing patient-oriented digital media file 182, a code configured to be inputted at a web site (or other wireless file server or file transfer protocol) for accessing patient-oriented digital media file 182, and an instruction for accessing patient-oriented digital media file 182 using a patient electronic device 122. Patient-oriented informational resource 180 and/or patient-oriented digital media file 182 may be transmitted to patient electronic device 122 and/or to patient local media library 126 from orthodontist electronic device 112, from orthodontist local media library 116, and/or from global media library 108.

Patient-oriented digital media file 182 may include and/or be any suitable digital media file that communicates one or more orthodontic instructions, which as discussed herein, may be orthodontic and/or dental home care instructions. As an example, patient-oriented digital media file 182 may include instructions regarding the proper cleaning of orthodontic braces, proper brushing and/or flossing of teeth to which orthodontic braces are attached, proper oral hygiene, the proper use of orthodontic rubber bands, head gear, and/or removable dental aligners (such as Invisalign® aligners).

Patient-oriented digital media file 182 may have any suitable format and/or may be in any suitable media for communication and/or access with the systems and methods disclosed herein. As examples, patient-oriented digital media file 182 may include and/or be a digital video file, a digital text file, a digital image file, a digital audio file, a portable document format file, a digital animation file, and/or a web site (or other file-sharing site) that lists, displays, and/or otherwise presents an orthodontic instruction. It is within the scope of the present disclosure that patient-oriented digital media file 182 may include and/or be a single digital media file or a plurality of digital media files.

Following the receipt of patient-oriented informational resource 180 by patient 120, communication infrastructure 104 may be configured to provide the orthodontist 110 with patient receipt information 190. The patient receipt information 190 may take the form of any suitable message that is based, at least in part, on the patient's interaction with patient-oriented informational resource 180 and/or patient-oriented digital media file 182. As an example, patient receipt information 190 may include data indicating if the patient 120 and/or the patient electronic device 122 has received the patient-oriented informational resource 180 and (optionally), if so, at what time the patient and/or the patient electronic device received the informational resource. The patient receipt information additionally or alternatively may further include data indicating if the patient has accessed the patient-oriented digital media file 182 corresponding to the patient-oriented informational resource 180 and (optionally), if so, at what time the patient accessed the digital media file. The patient receipt information and/or message may be indicated in any suitable format or medium. Examples include a text or email message, a change in font, boldness, or color of a portion of indicia or data on the user interface of the orthodontist's electronic device, etc.

It also is within the scope of the present disclosure that a patient 120 may utilize systems 100 and/or methods 200 according to the present disclosure to communicate orthodontic treatment information to orthodontist 110 and/or to dentist 160. For example, information transfer between patient 120, orthodontist 110, and/or dentist 160 may include a patient communication 198 that is delivered to orthodontist 110 via orthodontist electronic device 112 and/or that is delivered to dentist 160 via dentist electronic device 162 from patient 120 via patient electronic device 122. Patient communication 198 may include any appropriate information and/or communication regarding the patient's orthodontic and/or dental treatment, such as a text-based question and/or report, and/or a digital media file, such as an image file, video, and/or an audio file. For example, this information may include questions about the patient's orthodontic treatment plan and/or received (or expected) informational resources and/or digital media files. As another example, the orthodontic treatment information communicated between an orthodontist 110 and patient 120 (and/or dentist 160) may include information relating to the patient's treatment status, desired treatment result (e.g., teeth position and/or resulting smile), etc. As a more specific example, patient communication 198 may include a photograph of the patient's teeth, which may be delivered to orthodontist 110 via orthodontist electronic device 112 and/or to dentist 160 via dentist electronic device 162, who may then determine and/or revise an orthodontic and/or dental treatment plan and/or determine an orthodontic treatment instruction responsive to the patient's wishes and/or the state of the patient's teeth. Such a patient communication 198 additionally or alternatively may include information from the patient regarding the patient's desired smile (i.e., teeth alignment to produce a desired smile), which may be delivered to orthodontist 110 via orthodontist electronic device 112 and/or to dentist 160 via dentist electronic device 162, who may then determine and/or revise an orthodontic and/or dental treatment plan and/or determine an orthodontic treatment instruction responsive to the patient's wishes and/or the state of the patient's teeth.

It is within the scope of the present disclosure that caretaker 140 additionally or alternatively may receive the patient-oriented informational resource 180 that is delivered via communication infrastructure 104 and may access the corresponding patient-oriented digital media file 182. Patient-oriented informational resource 180 and/or patient-oriented digital media file 182 may be transmitted to caretaker electronic device 142 and/or to caretaker local media library 146 from orthodontist electronic device 112, from orthodontist local media library 116, and/or from global media library 108. Additionally, it is within the scope of the present disclosure that the caretaker 140 also may receive the patient receipt information 190 and/or that the orthodontist 110 may receive the patient receipt information 190 from the caretaker 140.

Additionally or alternatively, it is within the scope of the present disclosure that communication infrastructure 104 may facilitate information transfer between an orthodontist 110 and a dentist 160. Dentist 160 may receive a dentist-oriented informational resource 184 via communication infrastructure 104, with the dentist-oriented informational resource 184 being selected and/or provided by orthodontist 110. The dentist-oriented informational resource 184 may include a dentist-oriented digital media file 186 or a provision for accessing the dentist-oriented digital media file 186. The dentist-oriented digital media file 186 is configured to communicate dental instructions to the dentist regarding patient 120. These dental instructions may include instructions and/or recommendations for dental care or treatment, the previously described orthodontic instructions, and/or other information and/or requests to be communicated between orthodontist 110 and dentist 160.

Following the receipt of dentist-oriented informational resource 184 by dentist 160, the communication infrastructure may be configured to provide the orthodontist 110 with dentist receipt information 196. The dentist receipt information 196 may take the form of any suitable message that is based, at least in part, on the dentist's interaction with dentist-oriented digital media file 186. As an example, dentist receipt information 196 may include data indicating if the dentist has received the dentist-oriented informational resource 184 and (optionally), if so, at what time the dentist received the informational resource. The receipt information may further include data indicating if the dentist has accessed the dentist-oriented digital media file 186 corresponding to the dentist-oriented informational resource 184 and (optionally), if so, at what time the dentist accessed the digital media file. The message may take any suitable form, as discussed herein.

Dentist-oriented digital media file 186 may include and/or be any suitable digital media file that communicates one or more instructions for professional dental care for patient 120 that are based, at least in part, on an orthodontic treatment plan for patient 120 and/or a recent appointment, treatment, and/or other interaction between the patient and the orthodontist. As examples, dentist-oriented digital media file 186 may include suggestions regarding professional dental cleaning services, recommendations regarding specialty dental procedures, or instructions for an orthodontic assistant or technician. As additional examples, dentist-oriented digital media file 186 may include and/or be a digital video file, a digital text file, a digital image file, a digital audio file, a portable document format file, a digital animation file, and/or a web site (or other file-sharing site) that lists, displays, and/or otherwise presents a professional dental care instruction. It is within the scope of the present disclosure that dentist-oriented digital media file 186 may include and/or be a single digital media file or a plurality of digital media files. Dentist-oriented informational resource 184 and/or dentist-oriented digital media file 186 may be transmitted to dentist electronic device 162 and/or to dentist local media library 166 from orthodontist electronic device 112, from orthodontist local media library 116, and/or from global media library 108.

Additionally or alternatively, information transfer between orthodontist 110 and dentist 160 may pertain to referral information, such as referrals regarding proposed treatment plans and/or corresponding (current or prospective) dental health professionals relating to patient 120. For instance, an orthodontist 110 may deliver a message to a patient 120 and/or a dentist 160 not associated with the patient suggesting that the patient receive dental treatment from the dentist. Similarly, a dentist 160 may deliver a referral information resource 188 to a patient 120 and/or an orthodontist 110 not associated with the patient suggesting that the patient receive orthodontic treatment from the orthodontist. The referral information resource 188 may include contact information for the patient, dentist, and/or orthodontist, information regarding the recommended treatment, information regarding the patient's current status, etc. The patient information may include text, animations, x-rays, photographs, and/or other media relating to the past, current, and/or prospective state of the patient's teeth.

Figure 2:
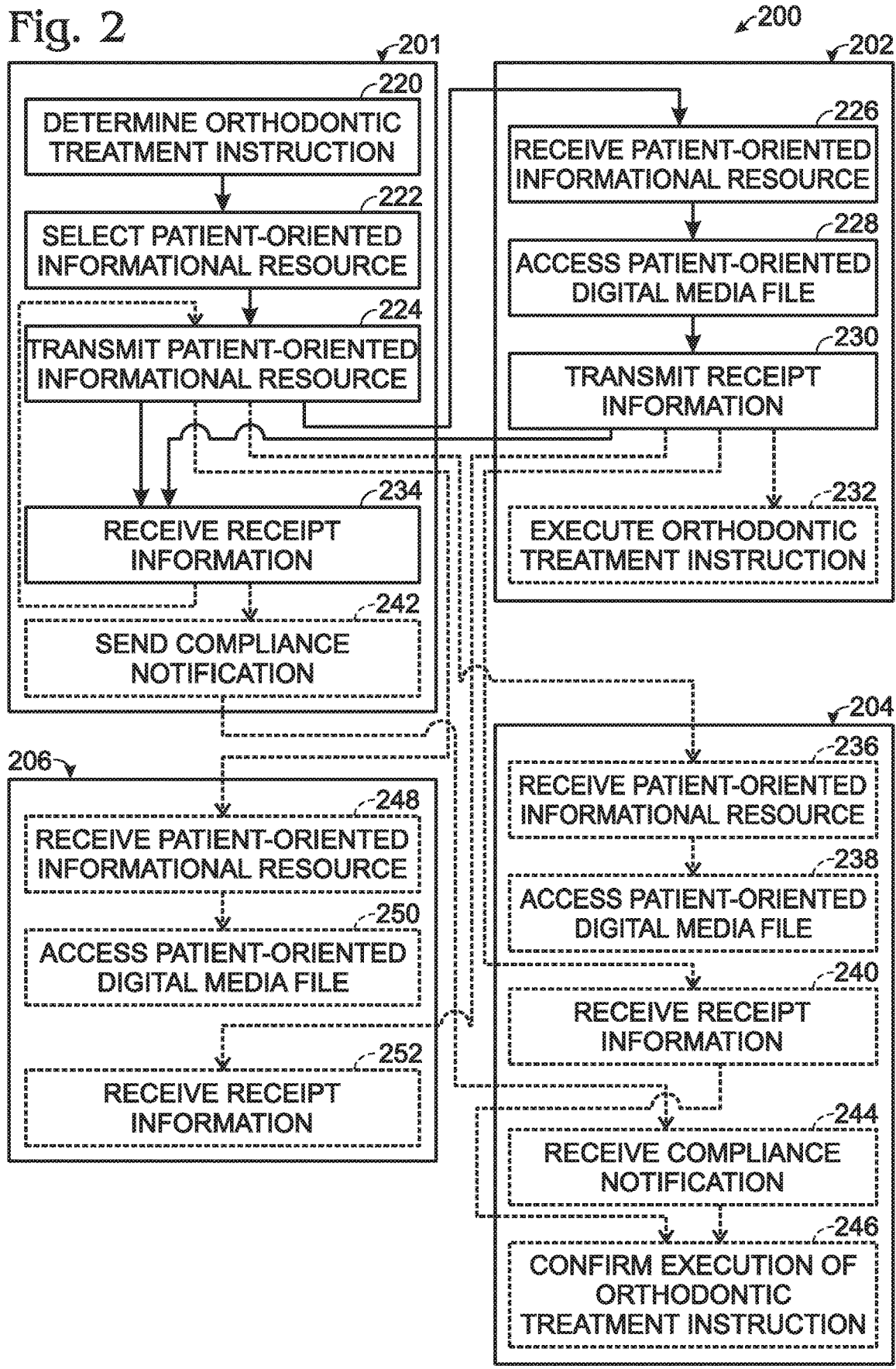
FIG. 2 is a flowchart schematically representing more specific examples of interactions, instructions, and/or types of information that may be transferred utilizing the systems and methods according to the present disclosure.

FIG. 2 generally and schematically illustrates examples of methods 200 according to the present disclosure. Additionally or alternatively, FIG. 2 may be described as generally and schematically illustrating the flow of information among an orthodontist 110, a patient 120, a caretaker 140, and a dentist 160 associated with systems 100 of FIG. 1. The flow chart schematically illustrates the general relationship between steps performed by one or more of the orthodontist, the patient, the caretaker, and/or the dentist, but such indications are not limiting in that such corresponding steps are not necessarily performed at a specific moment in time relative to other steps, and the relationships are depicted for illustrative purposes only.

Methods 200 according to the present disclosure may include one or more of a method 201 performed by orthodontist 110 and/or an associated orthodontist electronic device 112, a method 202 performed by patient 120 and/or an associated patient electronic device 122, a method 204 performed by caretaker 140 and/or an associated caretaker electronic device 142, and/or a method 206 performed by dentist 160 and/or an associated dentist electronic device 162. Additionally or alternatively, a method 200 may include steps performed by more than one of the orthodontist, the patient, the caretaker, and/or the dentist (or electronic devices associated therewith).

Moreover, the various illustrated steps in FIG. 2 are not all required for a given method 200, and methods 200 may include any suitable combination of the various steps illustrated in FIG. 2 and discussed herein. As used herein, reference to one or more of orthodontist 110, patient 120, caretaker 140, and/or dentist 160 inherently may include reference to an associated electronic device, such as may be operated by, for, and/or under the control of a respective person or organization. For example, with reference to FIG. 2, the transmitting indicated at 224, in which an orthodontist 110 transmits a patient-oriented informational resource 180 to one or more of a patient 120, a caretaker 140, and/or a dentist 160, optionally via an information router 105, also may be described from the perspective of orthodontist electronic device 112 as sending the digital media file to the patient 120, the caretaker 140, the dentist 160, and/or any associated electronic device thereof.

As indicated at 220 in FIG. 2, a method 200 may include orthodontist 110 determining a treatment instruction for a patient 120, wherein the treatment instruction is configured to be carried out by the patient 120. The treatment instruction may be an instruction that is specifically relevant to a particular patient 120 or may be an instruction that is broadly relevant to any of a plurality of patients. The choice of the treatment instruction may be, but is not required to be, responsive to an identified need, as determined at a recent orthodontic appointment and/or by the patient's treatment plan. As examples, the treatment instruction may refer to methods for cleaning teeth and/or orthodontic hardware configured to interface with the teeth, or methods for using and replacing orthodontic appliances such as rubber bands, orthodontic wax, and/or head gear.

Subsequent to the determining the treatment instruction indicated at 220, the orthodontist 110 may select a patient-oriented informational resource 180 corresponding to a patient-oriented digital media file 182 that in turn corresponds to the treatment instruction, as schematically indicated at 222 in FIG. 2. As mentioned, the patient-oriented digital media file 182 may take the form of any appropriate media file that is configured to communicate the treatment instruction to the patient 120. The orthodontist optionally may create the patient-oriented digital media file 182 anew (i.e., without basing it on a preexisting media file), may create the digital media file by editing an existing patient-oriented digital media file 182, or may select the patient-oriented digital media file 182 from a library of preexisting digital media files. For example, orthodontist 110 may select the patient-oriented digital media file 182 from global media library 108 and/or from orthodontist local media library 116. The orthodontist may then transmit a patient-oriented informational resource 180 to the patient 120, as schematically indicated at 224 in FIG. 2, wherein the patient-oriented informational resource 180 may include and/or be a provision for accessing the patient-oriented digital media file 182, or may be the patient-oriented digital media file 182.

As schematically indicated at 226 in FIG. 2, a method 202 associated with patient 120 may include receiving the patient-oriented informational resource 180 from the orthodontist 110. The receiving the patient-oriented informational resource may include any interaction between the patient 120 and the patient-oriented informational resource 180, which may take place via patient electronic device 122 associated with patient 120. As an example, and as indicated at 226 in FIG. 2, method 202 may include the patient 120 opening and/or reading a message that includes patient-oriented informational resource 180. Subsequent to receiving the informational resource, the patient 120 may access the patient-oriented digital media file 182 associated with patient-oriented informational resource 180, as indicated schematically at 228 in FIG. 2. As examples, the patient-oriented digital media file may be included in, and/or accessible from, the patient-oriented informational resource, and/or may be stored in patient local media library 126. Additionally or alternatively, accessing the patient-oriented digital media file may include the patient following an Internet link included in patient-oriented informational resource 180 and/or using an access code provided in patient-oriented informational resource 180 to retrieve a patient-oriented digital media file 182 from a web site and/or from global media library 108.

Patient-oriented informational resource 180 and/or the associated patient-oriented digital media file 182 may correspond to patient receipt information 190. Patient receipt information 190 may include data indicating if the patient 120 and/or the patient electronic device 122 has received the informational resource as indicated at 226 and optionally may further include data indicating what time (i.e., when) the patient and/or the patient electronic device received the informational resource if the informational resource was received by the patient. Patient receipt information 190 additionally or alternatively may include data indicating if the patient 120 has accessed the patient-oriented digital media file 182 as indicated at 228 and optionally may further include data indicating at what time (i.e., when) the patient accessed the digital media file if the patient accessed the digital media file.

As indicated schematically at 230 in FIG. 2, the method 202 may further include transmitting the patient receipt information 190 to the orthodontist 110, the caretaker 140, and/or the dentist 160. The patient receipt information may be transmitted responsive to receipt and/or access of the informational resource and/or digital media file.

As another example, the patient receipt information 190 may be available to the orthodontist 110, to the caretaker 140, and/or to the dentist 160 as soon as the corresponding informational resource is transmitted from the orthodontist to the patient (and hence before the patient receives the informational resource), in which case the transmission of receipt information indicated at 230 may take place if and when the patient receives the patient-oriented informational resource 180 and/or accesses the corresponding patient-oriented digital media file 182. Stated another way, as soon as the orthodontist 110 transmits the patient-oriented informational resource 180 to the patient 120 (and optionally to the caretaker 140 and/or the dentist 160), the patient receipt information 190 may be created simultaneously and indicate that the patient 120 has neither received the patient-oriented informational resource 180 nor accessed the corresponding patient-oriented digital media file 182. In this case, the transmission of the receipt information schematically indicated at 230 in FIG. 2 may correspond to the patient receipt information 190 changing its state upon an interaction between the patient 120 and the patient-oriented informational resource 180, with this change of state being visible to one or more of the orthodontist, the caretaker, and/or the dentist. As indicated schematically at 232 in FIG. 2, the patient 120 may then optionally execute the orthodontic instruction specified by the patient-oriented digital media file 182.

As indicated schematically at 234 in FIG. 2, the orthodontist 110 may choose to view the patient receipt information 190 at any time following the transmission of the patient-oriented informational resource 180. Based upon the data indicated by the patient receipt information and optionally the interval of time separating the transmission of the patient-oriented informational resource and the viewing of the patient receipt information, the orthodontist may choose to repeat the transmission of the patient-oriented informational resource to the patient. For instance, if the patient receipt information 190 indicates that the patient 120 has not received the patient-oriented informational resource 180 and/or accessed the patient-oriented digital media file 182 within a predetermined time interval, the orthodontist 110 may repeat the sending the patient-oriented informational resource in an effort to encourage compliance by the patient. The predetermined time interval may be any appropriate length of time and/or may be determined by any appropriate individual. As examples, the predetermined time interval may be at most one day, at most one week, at most two weeks, at most one month at most six months, and/or at most one year, and/or may be determined by the orthodontist 110, by the caretaker 140, or by the dentist 160. Additionally or alternatively, if the patient receipt information 190 indicates that the patient 120 has not received the patient-oriented informational resource 180 and/or accessed the patient-oriented digital media file 182 within the predetermined time interval (such as since a prior transmission of the informational resource and/or since the patient's most recent appointment with the orthodontist), the orthodontist 110 may send a compliance notification 192 to caretaker 140. The compliance notification 192 may be any suitable message that indicates that the patient 120 has not yet received the patient-oriented informational resource 180 or accessed the patient-oriented digital media file 182.

Methods 200 may further include methods 204 associated with caretaker 140. As indicated schematically at 236 in FIG. 2, the caretaker 140 also may receive the patient-oriented informational resource 180 that is transmitted from the orthodontist 110 to the patient 120, and may subsequently access the associated patient-oriented digital media file 182, as indicated at 238. In this way, the caretaker 140 may be informed of the orthodontic care instructions that are being delivered to the patient by the orthodontist, and optionally help to encourage, instruct, and/or require that such instructions are accessed and followed by the patient. As indicated schematically at 240, the caretaker also may receive the patient receipt information 190 that reflects whether and when the patient 120 has received the patient-oriented informational resource 180 and/or accessed the corresponding patient-oriented digital media file 182. Additionally, as indicated schematically at 244, the caretaker may receive a compliance notification 192 that is sent by the orthodontist 110 in the event that the orthodontist deems the receipt information 190 to be unsatisfactory. Responsive to the data contained in the patient receipt information 190 and/or the compliance notification 192 provided by the orthodontist 110, the caretaker 140 may confirm the execution of the treatment instruction by the patient 120.

Methods 200 may further include methods 206 associated with a dentist 160. As indicated schematically at 248 in FIG. 2, the dentist 160 also may receive the patient-oriented informational resource 180 that is transmitted from the orthodontist 110 to the patient 120, and may subsequently access the associated patient-oriented digital media file 182, as indicated at 250. In this way, the dentist 160 may be informed of the orthodontic care instructions that are being delivered to the patient by the orthodontist, and so gain a more complete understanding of the patient's orthodontic treatment plan. As indicated schematically at 252, the dentist also may receive the patient receipt information 190 that indicates whether (and optionally when) the patient 120 has received the patient-oriented informational resource 180 and/or accessed the corresponding patient-oriented digital media file 182.

FIG. 3 generally and schematically illustrates examples of methods 300. Additionally or alternatively, FIG. 3 may be described as generally and schematically illustrating the optional flow of information among an orthodontist 110 and a dentist 160 regarding a patient 120 of each the orthodontist and the dentist. The flow chart schematically illustrates the general relationship between steps performed by one or more of the orthodontist and the dentist, but such indications are not limiting in that such corresponding steps are not necessarily performed at a specific moment in time relative to other steps, and the relationships are depicted for illustrative purposes only.

Methods 300 according to the present disclosure may include one or more of a method 301 performed by an orthodontist 110 and/or an associated orthodontist electronic device 112 and/or a method 306 performed by a dentist 160 and/or an associated dentist electronic device 162. Additionally or alternatively, a method 300 may include steps performed by both the orthodontist and the dentist. Moreover, the various illustrated steps in FIG. 3 are not required for a given method 300, and methods 300 may include any suitable combination of the various optional steps illustrated in FIG. 3 and discussed herein.

As indicated at 320 in FIG. 3, a method 300 may include orthodontist 110 determining a treatment instruction for a patient 120, wherein the treatment instruction is configured to be carried out by the dentist 160. As examples, the treatment instruction may refer to a personalized dental cleaning instruction to be carried out by a general practice dentist, a recommendation for a surgical procedure to be carried out by an oral surgeon, or instructions for creating an orthodontia-compatible dental prosthesis to be placed by a prosthodontist.

Subsequent to the determining the treatment instruction indicated at 320, the orthodontist 110 may select a dentist-oriented informational resource 184 corresponding to a dentist-oriented digital media file 186 that in turn corresponds to the treatment instruction, as schematically indicated at 322 in FIG. 3. The dentist-oriented digital media file 186 may take the form of any appropriate media file that is configured to communicate the treatment instruction to the dentist 160. The orthodontist may create the dentist-oriented digital media file 186 anew (i.e., without basing it on a preexisting media file), may edit an existing digital media file, and/or may select the dentist-oriented digital media file 186 from a library of preexisting digital media files. For example, orthodontist 110 may select the dentist-oriented digital media file 186 from global media library 108 and/or from orthodontist local media library 116. The orthodontist may then transmit dentist-oriented informational resource 184 to the dentist 160, as schematically indicated at 324 in FIG. 3. The dentist-oriented informational resource 184 may include a provision for accessing the dentist-oriented digital media file 186, or may be or include the dentist-oriented digital media file 186.

As schematically indicated at 326 in FIG. 3, a method 306 associated with dentist 160 may include receiving the dentist-oriented informational resource 184 from the orthodontist 110. The receiving the dentist-oriented informational resource may include any interaction between the dentist 160 and the dentist-oriented informational resource 184, which may take place via dentist electronic device 162 associated with dentist 160. As an example, and as indicated at 326 in FIG. 3, method 306 may include the dentist 160 opening and/or reading a message that includes dentist-oriented informational resource 184. Subsequent to receiving the informational resource, the dentist 160 may access the dentist-oriented digital media file 186 associated with dentist-oriented informational resource 184, as indicated schematically at 328 in FIG. 3. As examples, the dentist-oriented digital media file may be included in, and/or accessible from, the dentist-oriented informational resource, and/or may be stored in dentist local media library 166. Additionally or alternatively, accessing the dentist-oriented digital media file 186 may include the dentist following an Internet link included in dentist-oriented informational resource 184 and/or using an access code provided in dentist-oriented informational resource 184 to retrieve a dentist-oriented digital media file 186 from a web site and/or from global media library 108.

Dentist-oriented informational resource 184 and the associated dentist-oriented digital media file 186 may have corresponding dentist receipt information 196, wherein the dentist receipt information includes data indicating if (and/or when) the dentist 160 has received the informational resource, as indicated at 326. Dentist receipt information 196 additionally or alternatively may include data indicating if and/or when the dentist 160 has accessed the dentist-oriented digital media file 186, as indicated schematically at 328. The dentist receipt information may be transmitted responsive to receipt and/or access of the dentist-oriented informational resource and/or the dentist-oriented digital media file.

As another example, the dentist receipt information 196 may be available to the orthodontist 110 as soon as the corresponding dentist-oriented informational resource is transmitted from the orthodontist to the dentist (and hence before the dentist receives the dentist-oriented informational resource), in which case the transmission of receipt information indicated at 330 may take place if and when the dentist receives the dentist-oriented informational resource 184 and/or accesses the corresponding dentist-oriented digital media file 186. Stated another way, responsive to the orthodontist 110 transmitting the dentist-oriented informational resource 184 to the dentist 160, the dentist receipt information 196 may be created simultaneously and indicate that the dentist 160 has neither received the dentist-oriented informational resource 184 nor accessed the corresponding dentist-oriented digital media file 186. In this case, the transmission of the receipt information schematically indicated at 330 in FIG. 3 may correspond to the dentist receipt information 196 changing its state upon an interaction between the dentist 160 and the dentist-oriented informational resource 184, with this change of state being visible to the orthodontist. As indicated schematically at 332 in FIG. 3, the dentist 160 then may optionally execute the instruction specified by the dentist-oriented digital media file 186.

As indicated schematically at 334 in FIG. 3, the orthodontist 110 may choose to view the dentist receipt information 196 at any time following the transmission of the dentist-oriented informational resource 184. Based upon the data indicated by the dentist receipt information and the interval of time separating the transmission of the dentist-oriented informational resource and the viewing of the dentist receipt information, the orthodontist may choose to repeat the transmission of the dentist-oriented informational resource to the dentist. For instance, if the dentist receipt information 196 indicates that the dentist 160 has not received the dentist-oriented informational resource 184 and/or accessed the dentist-oriented digital media file 186 within a predetermined time interval (such as after the informational resource was first or previously sent and/or accessed), the orthodontist 110 may repeat the sending the dentist-oriented informational resource in an effort to ensure receipt and access of the dental instruction by the dentist 160.

The treatment instruction additionally may include a referral of the patient from the orthodontist to the dentist 160, or a referral of the patient from the dentist to the orthodontist 110. When utilized to provide a referral, the treatment instruction may include contact information for the patient, the orthodontist, and/or the dentist. The treatment instruction also may include information and/or at least one digital media file regarding the desired treatment, the patient's treatment plan, and/or the patient's prior, current, and/or prospective dental status. Patient 120 and/or caregiver 140 additionally may be provided with a notice of the referral, the treatment instruction and/or a prior request to consent to the referral and/or sending of the treatment instructions.

FIG. 4 generally and schematically represents an example of a graphical interface for an orthodontist 110 according to the present disclosure. An orthodontist graphical interface 114 may take the form of any suitable display, such as presented on a display screen or other orthodontist graphical interface 114 of an orthodontist electronic device 112 associated with orthodontist 110. The orthodontist graphical interface 114 may be configured to present the orthodontist 110 with a plurality of modules for accessing various resources relating to systems and methods according to the present disclosure. As used herein, modules for accessing various resources additionally or alternatively may be described as tabs, panels, windows, screens, and/or buttons for accessing various resources, and such terms are intended to serve as examples of provisions for accessing various resources displayed on an electronic interface.

With reference to FIG. 4, orthodontist graphical interface 114 may provide access to a patients module 410, a media module 430, a resources module 450, and/or any additional modules corresponding to any systems or methods according to the present disclosure. The patients module 410 may provide the orthodontist 110 with access to a patient directory 412, a new patient interface 414, a list of referred patients 416, and/or a list of flagged patients 418. Each of the patient directory 412, the new patient interface 414, the list of referred patients 416, and the list of flagged patients 418 may include and/or provide access to one or more patient overviews 400.

The patient directory 412 may take the form of an ordered list, a database, and/or any other suitable data structure that is configured to store and display patient overview 400. As illustrated in more detail in FIG. 8, patient overview 400 may include patient data 402 corresponding to one or more patients 120 of the orthodontist 110. Patient overview 400 may refer to a collection of all patient data 402 for a given patient 120, and/or may refer to a graphical presentation of the collection of all patient data 402 for the given patient. The patient data 402 for a particular patient 120 may include the patient's name, the patient's date of birth, the patient's contact information, the name and/or contact information of the patient's caretaker 140, the name and/or contact information of the patient's dentist 160, comments regarding the patient, and/or a list of digital media files 182 that have been sent to the patient 120 (by proxy of corresponding informational resources 180), optionally including the corresponding receipt information 190. When displaying the patient data 402 corresponding to a particular patient 120, the display panel may additionally present the orthodontist 110 with the ability to transmit a patient-oriented informational resource 180 to patient 120 and/or send an electronic message to patient 120.

The new patient interface 414 is configured to permit the orthodontist 110 to add a new patient 120 to the patient directory 412. The list of referred patients 416 may provide the orthodontist 110 with a list of patients that have been referred to the orthodontist by a dentist 160 associated with the referred patient. The patients listed in the list of referred patients 416 may be patients 120 who are already under the care of orthodontist 110, and or may be patients who have not yet engaged the services of orthodontist 110. The list of flagged patients 418 may provide the orthodontist 110 with a list of patients 120 who may need a form of prioritized attention. For example, the patients 120 in the list of flagged patients 418 may be patients with corresponding patient receipt information 190 indicating a failure to receive and/or view a patient-oriented informational resource 180 and/or a patient-oriented digital media file 182. Additionally or alternatively, the patients 120 in the list of flagged patients 418 may be patients who are overdue for an appointment with orthodontist 110, whose corresponding patient overview 400 is lacking one or more items of patient data 402, and/or who have provided a patient communication 198 to orthodontist 110.

Media module 430 of orthodontist graphical interface 114 may provide access to an orthodontist local media interface 432, a global media interface 434, and an orthodontist media upload interface 436. Orthodontist local media interface 432 may be a graphical interface for accessing, viewing, manipulating, and/or selecting one or more digital media files from orthodontist local media library 116. Similarly, global media interface 434 may be a graphical interface for accessing, viewing, manipulating, and/or selecting one or more patient-oriented digital media files 182 and/or dentist-oriented digital media files 186 from global media library 108. Orthodontist local media interface 432 and/or global media interface 434 may permit the orthodontist 110 to deliver a selected digital media file directly to patient 120 and/or dentist 160. Media upload interface 436 may permit the orthodontist 110 to add a new patient-oriented digital media file 182 and/or a new dentist-oriented digital media file 186 to global media library 108 and/or to orthodontist local media library 116. Orthodontist local media interface 432 and/or global media interface 434 may take the form of an ordered list, a database, and/or any other suitable data structure that is configured to store and display representations 183 of one or more digital media files. For example, representation 183 of a patient-oriented digital media file 182 may include a title, an icon, a thumbnail image, a brief description, one or more descriptive tags, and/or any additional or alternative descriptor for the patient-oriented digital media file 182. Additionally or alternatively, the representation 183 of a patient-oriented digital media file 182 may include and/or be a link for accessing the patient-oriented digital media file 182 and/or the corresponding patient-oriented informational resource 180 directly. Orthodontist local media interface 432 and/or global media interface 434 additionally or alternatively may include one or more categories and/or groupings of digital media files, which may be presented in separate windows and/or modules. For example, the categories and/or groupings of digital media files may permit the orthodontist 110 to sort the digital media files by intended recipient, by digital media file type, by topic, and/or by any other appropriate descriptor.

Resources module 450 of orthodontist graphical interface 114 may include one or more tools, resources, and/or information files regarding utilization of systems 100, of computer network 102, and/or of communication infrastructure 104 according to the present disclosure. For example, resources module 450 may include one or more tutorial videos regarding the utilization of systems 100, of computer network 102, and/or of communication infrastructure 104, and/or may include one or more advertising resources configured to facilitate the orthodontist 110 reaching out to additional patients 120, caretakers 140, and/or dentist 160, such as to invite participation in information coordination systems 100 according to the present disclosure.

Orthodontist graphical interface 114 also may include any additional modules to access, view, and/or manipulate information regarding patient 120, caretaker 140, and/or dentist 160. For example, and as illustrated in FIG. 4, orthodontist graphical interface 114 additionally may include a dentists module 460, which may include a list of dentists including dentist data corresponding to one or more dentists 160 associated with the one or more patients 120 of the orthodontist 110. The dentist data for a particular dentist 160 may include the dentist's name, the dentist's contact information, the names and/or contact information of the patients 110 associated with the dentist 160, comments regarding the dentist, and/or a list of digital media files 186 that have been sent to the dentist 160 (by proxy of corresponding dentist-oriented informational resource 184), optionally including the corresponding receipt information 196.

Orthodontist graphical interface 114 additionally may include an orthodontist messages module 470, such as which may provide the orthodontist 110 with access to a messages module, such as which may include an inbox and/or a messages outbox, and which may contain and/or otherwise provide access to electronic messages exchanged between the orthodontist 110 and any of patient 120, caretaker 140, and/or dentist 160. The orthodontist messages module 470 additionally may provide the orthodontist 110 with access to a message composition interface, with which the orthodontist 110 may compose and send an electronic message to any patient 120, caretaker 140, and/or dentist 160. Orthodontist messages module 470 additionally may include messages and/or other indicia or indicators relating to receipt information and/or the status thereof.

It also is within the scope of the present disclosure that the orthodontist 110 may exchange electronic messages with an additional orthodontist. Examples of such communications may pertain to sharing thoughts and/or strategies relating to interesting and/or challenging patient cases, communicating recommendations regarding dentists 160, and discussing general orthodontic tools and/or techniques.

Figure 5:
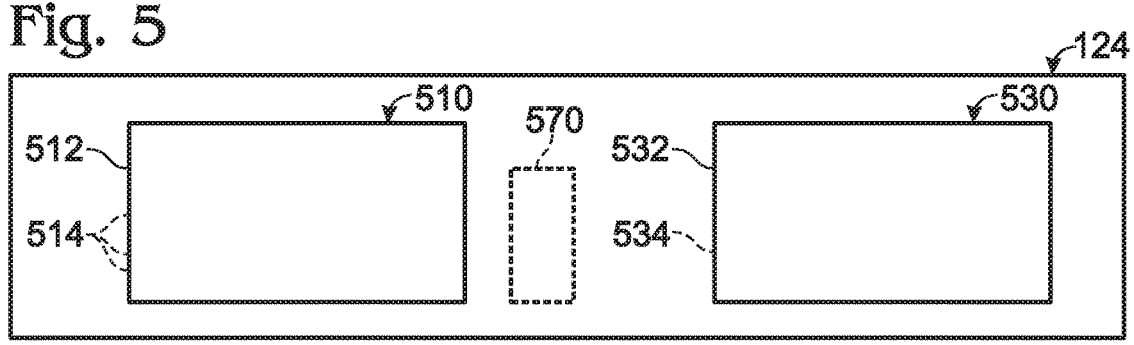
FIG. 5 is a schematic representation of a graphical interface for an orthodontic patient according to the present disclosure.

FIG. 5 generally and schematically represents an example of a patient graphical interface 124 for a patient 120 of an orthodontist 110 according to the present disclosure. Patient graphical interface 124 may take the form of any suitable display or other patient graphical interface 124 presented by a patient electronic device 122 associated with the patient 120. The patient graphical interface 124 may be configured to present the patient 120 with a plurality of modules for accessing various resources relating to systems and methods according to the present disclosure.

With reference to FIG. 5, patient graphical interface 124 may provide access to a doctors module 510, and a patient media module 530, and/or any additional modules corresponding to any systems or methods according to the present disclosure. The doctors module 510 of patient graphical interface 124 may include an orthodontist overview 512 and/or a dentist overview 514. The orthodontist overview 512 may include information pertaining to the orthodontist 110, examples of which may include the orthodontist's contact information and information regarding past or upcoming appointments with the orthodontist 110. The orthodontist overview 512 additionally may provide the patient 120 with an interface for exchanging messages with orthodontist 110 directly. Similarly, the dentist overview 514 may include information pertaining to the dentist 160, examples of which may include the dentist's contact information and information regarding past or upcoming appointments with the dentist 160, and additionally may include an interface for exchanging messages with dentist 160 directly. In some embodiments, the dentist 160 may refer to a plurality of dental healthcare professionals 160 associated with patient 120, in which case the dentist overview 514 may include a plurality of subpanels respectively corresponding to each of the plurality of dental healthcare professionals 160 associated with patient 120.

Patient media module 530 of patient graphical interface 124 may include a received media library 532 of patient-oriented informational resources 180 and/or of patient-oriented digital media files 182 that have been sent to the patient 120 from the orthodontist 110. The received media library 532 may take the form of an ordered list, a database, and/or any other suitable data structure that is configured to store and display representations 183 of one or more patient-oriented digital media files 182 corresponding to orthodontic treatment instructions. Patient media module 530 of patient graphical interface 124 additionally may include a media upload interface 534 configured to permit the patient 120 to upload a digital media file, such as a component of patient communication 198, to patient electronic device 122 and/or communication infrastructure 104.

Patient graphical interface 124 additionally may include a patient messages module 570 that may provide the patient 120 with access to a messages inbox and/or a messages outbox, which may correspond to electronic messages exchanged between the patient 120 and any of the associated orthodontist 110, caretaker 140, and/or dentist 160. The patient messages module 570 additionally may provide the patient 120 with access to a message composition interface, with which the patient 120 may compose and send an electronic message to the orthodontist 110, the caretaker 140, and/or the dentist 160.

Figure 6:
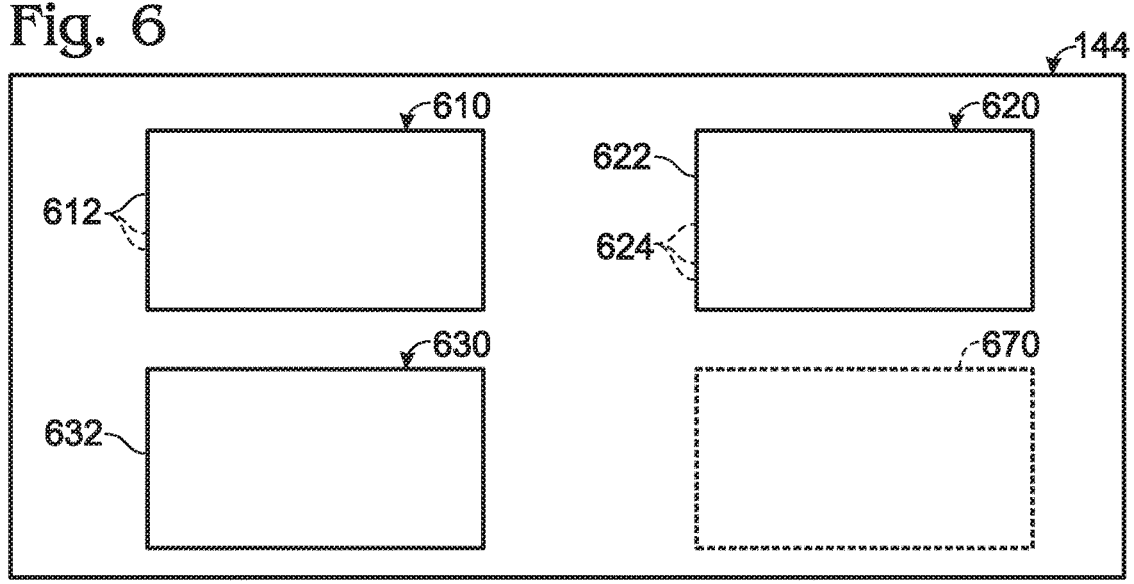
FIG. 6 is a schematic representation of a graphical interface for a dentist of an orthodontic patient according to the present disclosure.

FIG. 6 generally and schematically represents an example of a caretaker graphical interface 144 for a caretaker 140 of a patient 120 of an orthodontist 110 according to the present disclosure. Caretaker interface 144 may take the form of any suitable display or other caretaker graphical interface 144 presented by a caretaker electronic device 142 associated with the caretaker 140. The caretaker graphical interface 144 may be configured to present the caretaker 140 with a plurality of modules for accessing various resources relating to systems and methods according to the present disclosure.

With reference to FIG. 6, caretaker graphical interface 144 may provide access to a patients module 610, a doctors module 620, a caretaker media module 630, and/or any additional modules corresponding to any systems or methods according to the present disclosure. The patients module 610 of caretaker graphical interface 144 may include one or more patient overviews 612, which may include information pertaining to a corresponding one or more patients 120 of orthodontist 110 who are under the care of caretaker 140. The information contained in the one or more patient overviews 612 may include any appropriate information regarding the corresponding patients' orthodontic and/or dental treatment plan.

The doctors module 620 of caretaker graphical interface 144 may include an orthodontist overview 622 and/or a dentist overview 624. The orthodontist overview 622 may include information pertaining to the orthodontist 110, examples of which may include the orthodontist's contact information and information regarding a patient's past or upcoming appointments with the orthodontist 110. Similarly, the dentist overview 624 may include information pertaining to the dentist 160 of patient 120, examples of which may include the dentist's contact information and information regarding the patient's past or upcoming appointments with the dentist 160, and additionally may include an interface for exchanging messages with dentist 160 directly. In some embodiments, the dentist 160 may refer to a plurality of dental healthcare professionals 160 associated with patient 120, in which case the dentist overview 624 may include a plurality of subpanels respectively corresponding to each of the plurality of dental healthcare professionals 160 associated with patient 120 associated with caretaker 140.

Caretaker media module 630 of caretaker graphical interface 144 may include a received media library 632 of patient-oriented informational resources 180 and/or of patient-oriented digital media files 182 that have been sent to the patient 120 from the orthodontist 110. The received media library 632 may take the form of an ordered list, a database, and/or any other suitable data structure that is configured to store and display representations 183 of one or more patient-oriented digital media files 182 corresponding to orthodontic treatment instructions. Received media library 632 of caretaker media module 630 may be identical to received media library 532 of patient media module 530.

Caretaker graphical interface 144 additionally may include a caretaker messages module 670 that may provide the caretaker 140 with access to a messages inbox and/or a messages outbox, which may correspond to electronic messages exchanged between the caretaker 140 and any of the orthodontist 110, patient 120, and/or dentist 160. The caretaker messages module 670 additionally may provide the caretaker 140 with access to a message composition interface, with which the caretaker 140 may compose and send an electronic message to the orthodontist 110, the patient 120, and/or the dentist 160.

Figure 7:
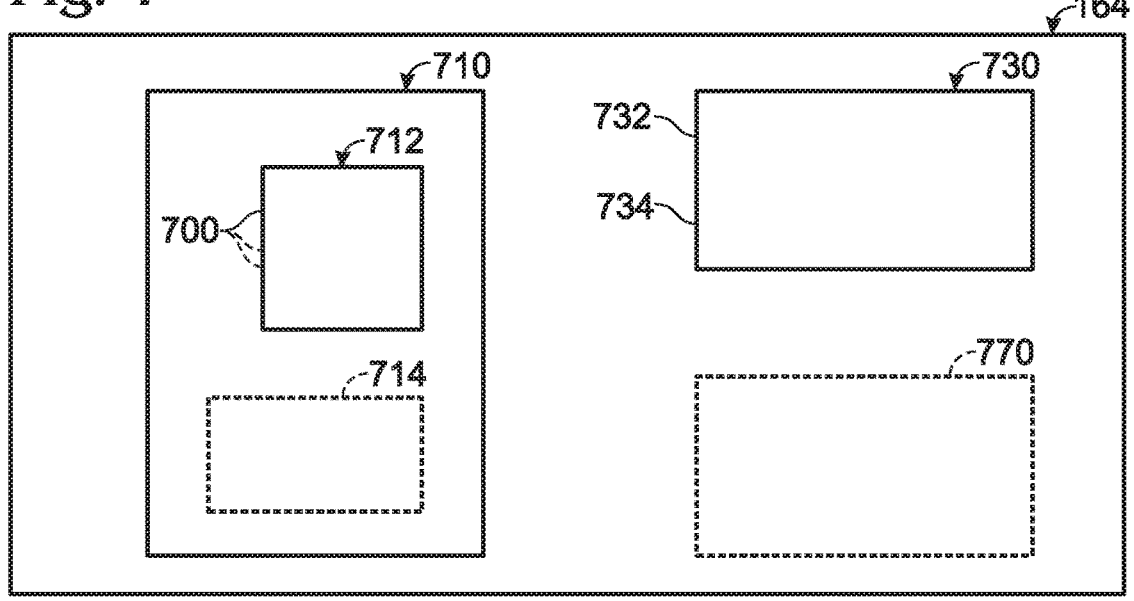
FIG. 7 is a schematic representation of a graphical interface for a caretaker of an orthodontic patient according to the present disclosure.

FIG. 7 generally and schematically represents an example of a dentist graphical interface 164 for a dentist 160 of a patient 120 according to the present disclosure. Dentist interface 164 may take the form of any suitable display or other dentist graphical interface 164 presented by a dentist electronic device 162 associated with the dentist 160. The dentist graphical interface 164 may be configured to present the dentist 160 with a plurality of modules for accessing various resources relating to systems and methods according to the present disclosure.

With reference to FIG. 7, dentist graphical interface 164 may provide access to a patients module 710, a dentist media module 730, and/or any additional modules corresponding to any systems or methods according to the present disclosure. The patients module 710 of dentist graphical interface 164 may include a patient directory 712, which may allow access to one or more patient overviews 700. A patient overview 700 may include information pertaining to a corresponding one or more patients 120 of dentist 160 and/or of orthodontist 110. The information contained in the one or more patient overviews 700 may include any appropriate information regarding the corresponding patients' orthodontic and/or dental treatment plan. The patients module 710 of dentist graphical interface 164 additionally may include a patient referral interface 714, which may be configured to permit the dentist 160 to refer a new patient to the orthodontist 110 and/or to receive a referral of a patient from the orthodontist 110.

Dentist media module 730 of dentist graphical interface 164 may provide access to a global media interface 732. Global media interface 732 may be a graphical interface for accessing, viewing, manipulating, and/or selecting one or more patient-oriented digital media files 182 and/or dentist-oriented digital media files 186 from global media library 108. Dentist media module 730 additionally may include a received media library 734 of patient-oriented informational resources 180 and/or of patient-oriented digital media files 182 that have been sent to the patient 120 and/or the dentist 160 from the orthodontist 110, and/or of dentist-oriented informational resources 184 and/or of dentist-oriented digital media files 186 that have been sent to the dentist 160 from the orthodontist 110. The received media library 734 may include and/or be an ordered list, a database, and/or any other suitable data structure that is configured to store and display representations 183 of one or more patient-oriented digital media files 182 corresponding to orthodontic treatment instructions. Additionally or alternatively, the received media library 734 may include and/or be an ordered list, a database, and/or any other suitable data structure that is configured to store and display representations 183 of one or more dentist-oriented digital media files 186.

Dentist graphical interface 164 additionally may include a dentist messages module 770 that may provide the dentist 160 with access to a messages inbox and/or a messages outbox, which may correspond to electronic messages exchanged between the dentist 160 and any of the orthodontist 110, patient 120, and/or caretaker 140. The dentist messages module 770 additionally may provide the dentist 160 with access to a message composition interface, with which the dentist 160 may compose and send an electronic message to the orthodontist 110, the patient 120, and/or the caretaker 140.

Figure 8:
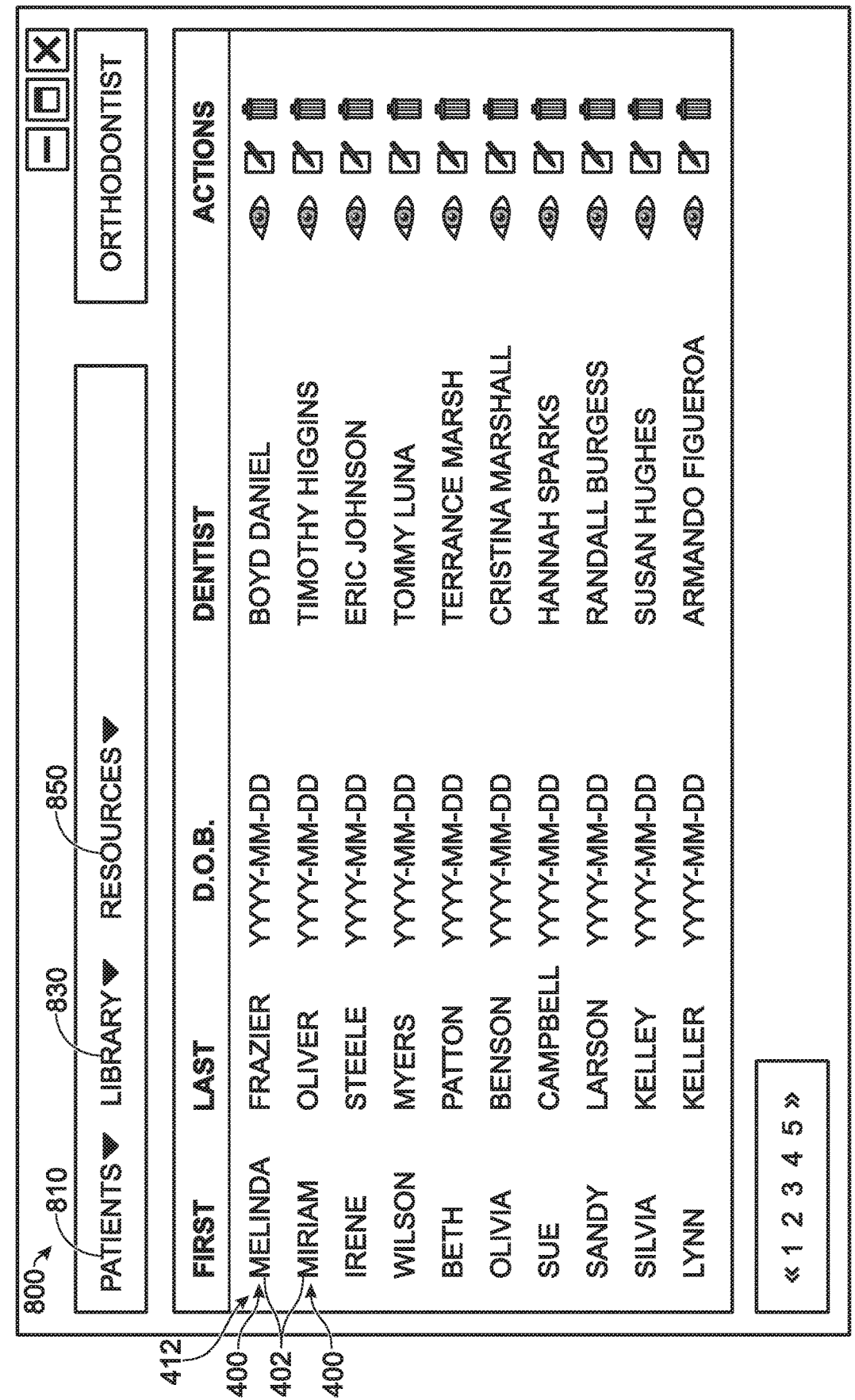
FIG. 8 is an example of a user interface that may be utilized with systems and/or methods according to the present disclosure.
Figure 9:
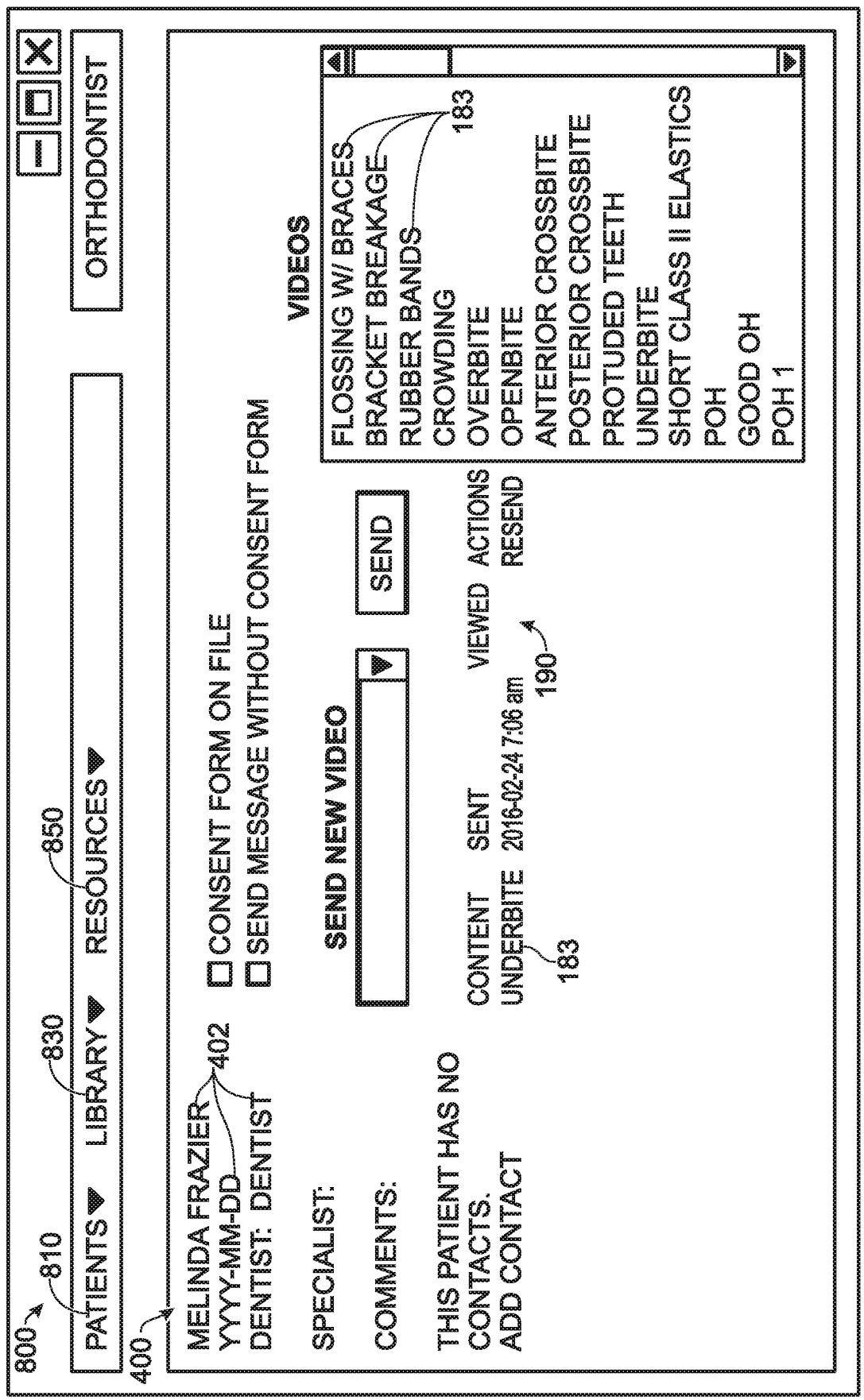
FIG. 9 is an additional example of a user interface that may be utilized with systems and/or methods according to the present disclosure.

FIGS. 8-10 display less schematic examples of an orthodontist graphical interface 114 and of modules of the orthodontist graphical interface 114 according to the present disclosure. With reference to each of FIGS. 8-10, orthodontist graphical interface 114 may include a plurality of tabs (or other pages, regions, links, and the like) 800 that may be configured to permit access to various sets of data, and may include a patients tab 810, a library tab 830, and/or a resources tab 850. The patients tab 810 may permit the orthodontist 110 to view a patient directory 412 that includes one or more patient overviews 400 corresponding to one or more of the orthodontist's patients 120. The library tab 830 may permit the orthodontist 110 to access the media module 430 and/or a component thereof such as orthodontist local media interface 432, global media interface 434, and/or orthodontist media upload interface 436. The resources tab 850 may permit the orthodontist 110 to access one or more tools, resources, and/or information files regarding utilization of systems 100, of computer network 102, and/or of communication infrastructure 104 according to the present disclosure.

FIG. 8 displays a less schematic example of a patient directory 412 within a patients module 410 according to the present disclosure. With reference to FIG. 8, a patient directory 412 may include one or more patient overviews 400 corresponding to one or more of the orthodontist's patients 120. Each patient overview 400 may include and/or display one or more items of patient data 402, as discussed. For example, and as illustrated in FIG. 8, each patient overview 400 displayed in patients module 410 may include a first name, a last name, a date of birth, and a dentist for each patient 120. Additionally or alternatively, each patient overview 400 displayed in patients module 410 may be an abbreviated patient overview that may include and/or be a link to access an expanded patient overview 400.

FIG. 9 displays a less schematic example of a patient overview 400 within a patients module 410 of an orthodontist graphical interface 114 according to the present disclosure. With reference to FIG. 9, a patient overview 400 may provide orthodontist 110 with an overview of any appropriate portion of available information pertaining to a given patient 120. For example, and as illustrated in FIG. 9, a patient overview 400 may include a plurality of items of patient information 402, such as the patient's name, the patient's date of birth, the patient's contact information, the name and/or contact information of the patient's caretaker 140, the name and/or contact information of the patient's dentist 160, comments regarding the patient, and/or a list of digital media files 182 that have been sent to the patient 120 (by proxy of corresponding informational resources 180), optionally including the corresponding receipt information 190. As illustrated in FIG. 9, patient overview 400 additionally may provide orthodontist 110 with an ability to select a representation 183 of a patient-oriented digital media file 182 from a list of representations and transmit the patient-oriented digital media file 182 and/or a corresponding patient-oriented informational resource 180 to the patient 120 without navigating away from the patient overview 400.

FIG. 10 displays a less schematic example of a media module 430 of an orthodontist graphical interface 114 according to the present disclosure, and in particular of a global media interface 434 of the media module 430. With reference to FIG. 10, a global media interface 434 may provide the orthodontist 110 with an overview of the digital media files available in global media library 108. Specifically, global media interface 434 may display one or more representations 183 of patient-oriented digital media files 182 that are stored in and/or provided by global media library 108. Each representation 183 may include a title, an icon, a thumbnail image, a brief description, and/or one or more descriptive tags corresponding to the patient-oriented digital media file 182. Additionally or alternatively, each representation 183 may include a link to permit the orthodontist 110 to add the corresponding patient-oriented digital media file 182 to the orthodontist local media library 116 and/or to add the corresponding digital media file to a dentist local media library 166.

The flowcharts and block diagrams described herein illustrate the architecture, functionality, and operation of possible implementations of systems, methods, and computer program products according to various illustrative embodiments. In this regard, each block in the flowcharts or block diagrams may represent a module, segment, or portion of code, which includes one or more executable instructions for implementing the specified logical function or functions. It should also be noted that, in some alternative implementations, the functions noted in a block may occur out of the order noted in the drawings. For example, the functions of two blocks shown in succession may be executed substantially concurrently, or the functions of the blocks sometimes may be executed in the reverse order, depending upon the functionality involved.

In the present disclosure, several of the examples have been discussed and/or presented in the context of flow diagrams, or flow charts, in which the methods are shown and described as a series of blocks, or steps. Unless specifically set forth in the accompanying description, it is within the scope of the present disclosure that the order of the blocks may vary from the illustrated order in the flow diagram, including with two or more of the blocks (or steps) occurring in a different order and/or concurrently. It also is within the scope of the present disclosure that the blocks, or steps, may be implemented as logic, which also may be described as implementing the blocks, or steps, as logics. In some applications, the blocks, or steps, may represent expressions and/or actions to be performed by functionally equivalent circuits or other logic devices. The illustrated blocks may, but are not required to, represent executable instructions that cause a computer, processor, and/or other logic device to respond, to perform an action, to change states, to generate an output or display, and/or to make decisions.

The subject matter disclosed herein is not limited to the field of orthodontic treatment and may be utilized in any suitable field in which coordinating information transfer, such as by coordinating instructions or procedures associated with a preferred method of performing a task, is desired. Examples include, but are not limited to, delivering home care instructions relating to other dental or medical fields such as dermatology, training workers to perform proper tasks and procedures, and delivering lessons and assignments to students.

As used herein, the term "and/or" placed between a first entity and a second entity means one of (1) the first entity, (2) the second entity, and (3) the first entity and the second entity. Multiple entries listed with "and/or" should be construed in the same manner, i.e., "one or more" of the entities so conjoined. Other entities may optionally be present other than the entities specifically identified by the "and/or" clause, whether related or unrelated to those entities specifically identified. Thus, as a non-limiting example, a reference to "A and/or B," when used in conjunction with open-ended language such as "comprising," may refer, in one embodiment, to A only (optionally including entities other than B); in another embodiment, to B only (optionally including entities other than A); in yet another embodiment, to both A and B (optionally including other entities). These entities may refer to elements, actions, structures, steps, operations, values, and the like.

As used herein, the phrase "at least one," in reference to a list of one or more entities, should be understood to mean at least one entity selected from any one or more of the entity in the list of entities, but not necessarily including at least one of each and every entity specifically listed within the list of entities and not excluding any combinations of entities in the list of entities. This definition also allows that entities may optionally be present other than the entities specifically identified within the list of entities to which the phrase "at least one" refers, whether related or unrelated to those entities specifically identified. Thus, as a non-limiting example, "at least one of A and B" (or, equivalently, "At least one of A or B," or, equivalently, "at least one of A and/or B") may refer, in one embodiment, to at least one, optionally including more than one, A, with no B present (and optionally including entities other than B); in another embodiment, to at least one, optionally including more than one, B, with no A present (and optionally including entities other than A); in yet another embodiment, to at least one, optionally including more than one, A, and at least one, optionally including more than one, B (and optionally including other entities). In other words, the phrases "at least one," "one or more," and "and/or" are open-ended expressions that are both conjunctive and disjunctive in operation. For example, each of the expressions "at least one of A, B, and C," "at least one of A, B, or C," "one or more of A, B, and C," "one or more of A, B, or C," and "A, B, and/or C" may mean A alone, B alone, C alone, A and B together, A and C together, B and C together, A, B, and C together, and optionally any of the above in combination with at least one other entity.

In the event that any patents, patent applications, or other references are incorporated by reference herein and (1) define a term in a manner that is inconsistent with and/or (2) are otherwise inconsistent with either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure that was present originally.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It also is within the scope of the present disclosure that elements, components, and/or other recited subject matter that is recited as being adapted to perform a particular function may additionally or alternatively be described as being configured to perform that function, and vice versa.

As used herein, the phrase "for example," the phrase "as an example," and/or simply the term "example," when used with reference to one or more components, features, details, structures, embodiments, and/or methods according to the present disclosure, are intended to convey that the described component, feature, detail, structure, embodiment, and/or method is an example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

Examples of systems and methods according to the present disclosure are presented in the following enumerated paragraphs. It is within the scope of the present disclosure that an individual step of a method recited herein, including in the following enumerated paragraphs, may additionally or alternatively be referred to as a "step for" performing the recited action.

A1. A method of electronically delivering orthodontic treatment instructions to a patient of an orthodontist, the method comprising:

selecting a patient-oriented informational resource responsive to an interaction between an orthodontist and a patient; and electronically transmitting the patient-oriented informational resource to the patient.

A2. The method of paragraph A1, wherein the method further includes electronically providing receipt information to the orthodontist, wherein the receipt information is based, at least in part, on an interaction between the patient and the patient-oriented informational resource.

A3. The method of any of paragraphs A1-A2, wherein the selecting the patient-oriented informational resource includes selecting from an electronic device that is configured to interact with the orthodontist.

A3.1. The method of paragraph A3, wherein the electronic device that is configured to interact with the orthodontist is a desktop computer.

A3.2. The method of paragraph A3, wherein the electronic device that is configured to interact with the orthodontist is a laptop computer.

A3.3. The method of paragraph A3, wherein the electronic device that is configured to interact with the orthodontist is a mobile electronic device.

A3.4. The method of paragraph A3, wherein the electronic device that is configured to interact with the orthodontist is a tablet computer.

A3.5. The method of paragraph A3, wherein the electronic device that is configured to interact with the orthodontist is a handheld electronic device.

A3.6. The method of paragraph A3, wherein the electronic device that is configured to interact with the orthodontist is a cellular/smart phone.

A4. The method of any of paragraphs A1-A3.6, wherein the patient-oriented informational resource corresponds to a determined orthodontic treatment instruction to be carried out by the patient.

A5. The method of any of paragraphs A1-A4, wherein the patient-oriented informational resource includes a provision for accessing a patient-oriented digital media file.

A5.1. The method of paragraph A5, wherein the provision includes, and optionally is, a link to a web site, a code configured to be inputted at a web site, and/or an instruction for accessing the patient-oriented digital media file via an electronic interface.

A6. The method of any of paragraphs A1-A5.1, wherein the patient-oriented informational resource includes a patient-oriented digital media file.

A7. The method of any of paragraphs A5-A6, wherein the patient-oriented digital media file includes one or more of a digital video file, a digital text file, a digital image file, a digital audio file, a portable document format file, and a digital animation file.

A8. The method of any of paragraphs A5-A7, wherein the patient-oriented digital media file is configured to communicate an instruction regarding the cleaning, use, and/or maintenance of orthodontic equipment and/or the cleaning of the patient's teeth.

A9. The method of paragraph A8, wherein the orthodontic equipment includes one or more of an orthodontic bracket, an orthodontic rubber band, an orthodontic retainer, orthodontic head gear, and orthodontic wax.

A10. The method of any of paragraphs A5-A9, wherein the patient-oriented digital media file is selected from a plurality of preexisting patient-oriented digital media files.

A11. The method of any of paragraphs A1-A9, wherein the patient-oriented informational resource is created after the determining the treatment instruction.

A12. The method of any of paragraphs A1-A11, wherein the electronically transmitting the patient-oriented informational resource to the patient includes electronically transmitting the patient-oriented informational resource to an electronic device that is owned by, possessed by, and/or previously selected or identified by the patient.

A13. The method of paragraph A12, wherein the electronic device of paragraph A12 is a desktop computer.

A13.1. The method of paragraph A12, wherein the electronic device of paragraph A12 is a laptop computer.

A13.2. The method of paragraph A12, wherein the electronic device of paragraph A12 is a mobile electronic device.

A13.3. The method of paragraph A12, wherein the electronic device of paragraph A12 is a tablet computer.

A13.4. The method of paragraph A12, wherein the electronic device of paragraph A12 is a handheld electronic device.

A13.5. The method of paragraph A12, wherein the electronic device of paragraph A12 is a cellular/smart phone.

A14. The method of any of paragraphs A1-A13.5, wherein the receipt information of paragraph A2 includes data indicating if the patient has received the patient-oriented informational resource.

A14.1. The method of any of paragraphs A1-A14, wherein the receipt information of paragraph A2 includes data indicating when the patient received the patient-oriented informational resource.

A15. The method of any of paragraphs A1-A14.1, wherein the receipt information of paragraph A2 includes data indicating if the patient has accessed a/the patient-oriented digital media file corresponding to the patient-oriented informational resource.

A15.1. The method of any of paragraphs A1-A15, wherein the receipt information of paragraph A2 includes data indicating when the patient accessed a/the patient-oriented digital media file corresponding to the patient-oriented informational resource.

A16. The method of any of paragraphs A1-A15.1, wherein the method further includes repeating the electronically transmitting the patient-oriented informational resource to the patient if the receipt information indicates that the patient has not received the patient-oriented informational resource and/or has not accessed a/the patient-oriented digital media file within a predetermined interval of time following a prior delivery of the patient-oriented informational resource to the patient.

A17. The method of any of paragraphs A1-A16, wherein the method further includes electronically providing a notification to a caretaker of the patient.

A18. The method of paragraph A17, when dependent on paragraph A2, wherein the electronically providing the notification to the caretaker of the patient occurs if the receipt information indicates that the patient has not received the patient-oriented informational resource and/or accessed a/the patient-oriented digital media file within a predetermined interval of time following a prior delivery of the patient-oriented informational resource to the patient.

A19. The method of any of paragraphs A17-A18, wherein the method further includes electronically providing the patient-oriented informational resource to the caretaker of the patient.

A19.1. The method of paragraph A19, wherein the electronically providing the patient-oriented informational resource to the caretaker includes electronically transmitting the patient-oriented informational resource to an electronic device that is owned by, possessed by, and/or previously selected or identified by the caretaker.

A19.2. The method of paragraph A19.1, wherein the electronic device of paragraph A19.1 is a desktop computer.

A19.3. The method of paragraph 19.1, wherein the electronic device of paragraph A19.1 is a laptop computer.

A19.4. The method of paragraph A19.1, wherein the electronic device of paragraph A19.1 is a mobile electronic device.

A19.5. The method of paragraph A19.1, wherein the electronic device of paragraph A19.1 is a tablet computer.

A19.6. The method of paragraph A19.1, wherein the electronic device of paragraph A19.1 is a handheld electronic device.

A19.7. The method of paragraph A19.1, wherein the electronic device of paragraph A19.1 is a cellular/smart phone.

A20. The method of any of paragraphs A17-A19.7, wherein the caretaker of the patient is at least one of a family member of the patient, a legal guardian of the patient, and an individual who is authorized to view the patient's orthodontic treatment records.

A21. The method of any of paragraphs A17-A20, when dependent on paragraph A2, wherein the method further includes electronically providing the receipt information to the caretaker.

A21.1. The method of paragraph A21, wherein the receipt information of paragraph A21 includes data indicating if the patient has received the patient-oriented informational resource.

A21.2. The method of any of paragraphs A21-A21.1, wherein the receipt information of paragraph A21 includes data indicating when the patient received the patient-oriented informational resource.

A21.3. The method of any of paragraphs A21-A21.2, wherein the receipt information of paragraph A21 includes data indicating if the patient has accessed a/the patient-oriented digital media file corresponding to the patient-oriented informational resource.

A21.4. The method of any of paragraphs A21-A21.3, wherein the receipt information of paragraph A21 includes data indicating when the patient accessed a/the patient-oriented digital media file corresponding to the patient-oriented informational resource.

A22. The method of any of paragraphs A1-A21.2, wherein the method further includes electronically providing an informational resource to a dentist.

A22.1. The method of paragraph A22, wherein the electronically providing the informational resource to the dentist includes electronically transmitting the informational resource to an electronic device that is configured to interact with the dentist.

A22.2. The method of paragraph A22.1, wherein the electronic device that is configured to interact with the dentist is a desktop computer.

A22.3. The method of paragraph A22.1, wherein the electronic device that is configured to interact with the dentist is a laptop computer.

A22.4. The method of paragraph A22.1, wherein the electronic device that is configured to interact with the dentist is a mobile electronic device.

A22.5. The method of paragraph A22.1, wherein the electronic device that is configured to interact with the dentist is a tablet computer.

A22.6. The method of paragraphs A22.1, wherein the electronic device that is configured to interact with the dentist is a handheld electronic device.

A22.7. The method of paragraph A22.1, wherein the electronic device that is configured to interact with the dentist is a cellular/smart phone.

A23. The method of any of paragraphs A22-A22.7, wherein the dentist is a general practice dentist associated with the patient.

A23.1. The method of any of paragraphs A22-A22.7, wherein the dentist is an orthodontic assistant associated with the patient.

A23.2. The method of any of paragraphs A22-A22.7, wherein the dentist is an oral surgeon associated with the patient.

A23.3. The method of any of paragraphs A22-A22.7, wherein the dentist is an endodontic specialist associated with the patient.

A23.4. The method of any of paragraphs A22-A22.7, wherein the dentist is a periodontist associated with the patient.

A23.5. The method of any of paragraphs A22-A22.7, wherein the dentist is a prosthodontist associated with the patient.

A24. The method of any of paragraphs A22-A23.5, wherein the informational resource is a dentist-oriented informational resource that corresponds to a determined treatment instruction for a patient of the orthodontist, wherein the treatment instruction is selected by the orthodontist to be executed by the dentist.

A25. The method of any of paragraphs A22-A23.5, wherein the informational resource is the patient-oriented informational resource that corresponds to a determined treatment instruction for a patient of the orthodontist, wherein the treatment instruction is selected by the orthodontist to be executed by the patient.

A26. The method of any of paragraphs A22-A25, wherein the method further includes electronically providing the receipt information to the dentist.

A26.1. The method of paragraph A26, wherein the receipt information of paragraph A26 includes data indicating if the patient has received the patient-oriented informational resource.

A26.2. The method of any of paragraphs A26-A26.1, wherein the receipt information of paragraph A26 includes data indicating when the patient received the patient-oriented informational resource.

A26.3. The method of any of paragraphs A26-A26.2, wherein the receipt information of paragraph A26 further includes data indicating if the patient has accessed a/the patient-oriented digital media file corresponding to the patient-oriented informational resource and, if so, at what time the patient accessed a/the patient-oriented digital media file.

A26.4. The method of any of paragraphs A26-A26.3, wherein the receipt information of paragraph A26 includes data indicating when the patient accessed a/the patient-oriented digital media file corresponding to the patient-oriented informational resource.

A27. The method of any of paragraphs A1-A26.4, wherein the method further includes electronically providing a/the dentist-oriented informational resource to a dentist.

A27.1. The method of paragraph A27, wherein the dentist-oriented informational resource provided to the dentist includes a referral for dental treatment.

A27.2. The method of any of paragraphs A27-A27.1, wherein the dentist-oriented informational resource provided to the dentist includes at least one of patient information and patient dental information.

A28. The method of any of paragraphs A1-A27.2, wherein the method includes receiving a referral informational resource from a dentist of the patient.

A28.1. The method of paragraph A28, wherein the referral informational resource received from the dentist includes a referral for orthodontic treatment.

A28.2. The method of any of paragraphs A28-A28.1, wherein the referral informational resource received from the dentist includes at least one of patient information and patient dental information.

A29. The method of any of paragraphs A1-A28.2, wherein the method includes receiving a patient communication from the patient regarding the patient's desired orthodontic treatment plan.

B1. A method of electronically delivering orthodontic treatment instructions to a patient of an orthodontist, the method comprising:
  selecting a patient from a list of patients;
  determining a treatment instruction for the patient;
  selecting a patient-oriented informational resource corresponding to the treatment instruction;
  electronically sending the patient-oriented informational resource to the patient; and
  receiving receipt information indicating if the patient has received the patient-oriented informational resource.

B1.1. The method of paragraph B1, wherein at least one of, and optionally both of, the determining and the selecting occur after an orthodontic appointment of the patient.

B1.2. The method of any of paragraphs B1-B1.1, wherein at least one of, and optionally both of, the determining and the selecting are responsive to a preexisting orthodontic treatment plan of the patient.

B2. The method of any of paragraphs B1-B1.2, wherein the receipt information includes data indicating if the patient has received the patient-oriented informational resource.

B2.1. The method of any of paragraphs B1-B2, wherein the receipt information of paragraph B1 includes data indicating when the patient received the patient-oriented informational resource.

B2.2. The method of any of paragraphs B1-B2.1, wherein the receipt information further includes data indicating if the patient has accessed the patient-oriented informational resource.

B2.3. The method of any of paragraphs B1-B2.2, wherein the receipt information of paragraph B1 includes data indicating when the patient accessed a patient-oriented digital media file corresponding to the patient-oriented informational resource.

B3. The method of any of paragraphs B1-B2.3, wherein the selecting the patient-oriented informational resource includes selecting from an electronic device that is configured to interact with the orthodontist.

B3.1. The method of paragraph B3, wherein the electronic device is a desktop computer.

B3.2. The method of paragraph B3, wherein the electronic device is a laptop computer.

B3.3. The method of paragraph B3, wherein the electronic device is a mobile electronic device.

B3.4. The method of paragraph B3, wherein the electronic device is a tablet computer.

B3.5. The method of paragraph B3, wherein the electronic device is a handheld electronic device.

B3.6. The method of paragraph B3, wherein the electronic device is a cellular/smart phone.

B4. The method of any of paragraphs B1-B3.6, wherein the patient-oriented informational resource corresponds to a determined orthodontic treatment instruction to be carried out by the patient.

B5. The method of any of paragraphs B1-B4, wherein the patient-oriented informational resource includes a provision for accessing a patient-oriented digital media file.

B5.1. The method of paragraph B5, wherein the provision is a link to a web site, a code configured to be inputted at a web site, and/or an instruction for accessing the patient-oriented digital media file via an electronic interface.

B6. The method of any of paragraphs B1-B5.1, wherein the patient-oriented informational resource includes a patient-oriented digital media file.

B7. The method of any of paragraphs B2.3 or B6, wherein the patient-oriented digital media file includes one or more of a digital video file, a digital text file, a digital image file, a digital audio file, a portable document format file, and a digital animation file.

B8. The method of any of paragraphs B2.3 or B6-B7, wherein the patient-oriented digital media file is configured to communicate an instruction regarding the cleaning, use, and/or maintenance of orthodontic equipment and/or the cleaning of the patient's teeth.

B9. The method of paragraph B8, wherein the orthodontic equipment includes one or more of an orthodontic bracket, an orthodontic rubber band, an orthodontic retainer, orthodontic head gear, and orthodontic wax.

B10. The method of any of paragraphs B2.3 or B6-B9, wherein the patient-oriented digital media file is selected from a plurality of preexisting patient-oriented digital media files.

B11. The method of any of paragraphs B2.3 or B6-B10, wherein the patient-oriented digital media file is created after the determining the treatment instruction.

B12. The method of any of paragraphs B1-B11, wherein the electronically sending the patient-oriented informational resource to the patient includes electronically transmitting the patient-oriented informational resource to an electronic device that is owned by, possessed by, and/or previously selected or identified by the patient.

B13. The method of paragraph B12, wherein the electronic device of paragraph B12 is a desktop computer.

B13.1. The method of paragraph B12, wherein the electronic device of paragraph B12 is a laptop computer.

B13.2. The method of paragraph B12, wherein the electronic device of paragraph B12 is a mobile electronic device.

B13.3. The method of paragraphs B12, wherein the electronic device of paragraph B12 is a tablet computer.

B13.4. The method of paragraph B12, wherein the electronic device of paragraph B12 is a handheld electronic device.

B13.5. The method of paragraph B12, wherein the electronic device of paragraph B12 is a cellular/smart phone.

B14. The method of any of paragraphs B1-B13.5, wherein the method further includes repeating the electronically sending the patient-oriented informational resource to the patient if the receipt information indicates that the patient has not received the patient-oriented informational resource and/or accessed a/the patient-oriented digital media file within a predetermined interval of time following a prior delivery of the patient-oriented informational resource to the patient.

B15. The method of any of paragraphs B1-B14, wherein the method further includes electronically providing a notification to a caretaker of the patient.

B16. The method of paragraph B15, wherein the electronically providing the notification to the caretaker of the patient occurs if the receipt information indicates that the patient has not received the patient-oriented informational resource and/or accessed a/the patient-oriented digital media file within a predetermined interval of time following a prior delivery of the patient-oriented informational resource to the patient.

B17. The method of any of paragraphs B15-B16, wherein the method further includes electronically sending the patient-oriented informational resource to the caretaker of the patient.

B17.1. The method of paragraph B17, wherein the electronically sending the patient-oriented informational resource to the caretaker includes electronically transmitting the patient-oriented informational resource to an electronic device that is owned by, possessed by, and/or previously selected or identified by the caretaker.

B17.2. The method of paragraph B17.1, wherein the electronic device of paragraph B17.1 is a desktop computer.

B17.3. The method of paragraph B17.1, wherein the electronic device of paragraph B17.1 is a laptop computer.

B17.4. The method of paragraph B17.1, wherein the electronic device of paragraph B17.1 is a mobile electronic device.

B17.5. The method of paragraph B17.1, wherein the electronic device of paragraph B17.1 is a tablet computer.

B17.6. The method of paragraph B17.1, wherein the electronic device of paragraph B17.1 is a handheld electronic device.

B17.7. The method of paragraph B17.1, wherein the electronic device of paragraph B17.1 is a cellular/smart phone.

B18. The method of any of paragraphs B15-B17.7, wherein the caretaker of the patient is at least one of a family member of the patient, a legal guardian of the patient, and an individual who is authorized to view the patient's orthodontic treatment records.

B19. The method of any of paragraphs B1-B18, wherein the method further includes electronically providing the receipt information to a/the caretaker of the patient.

B20. The method of any of paragraphs B1-B19, wherein the method further includes electronically sending an informational resource to a dentist.

B20.1. The method of paragraph B20, wherein the electronically sending the informational resource to the dentist includes electronically transmitting the informational resource to an electronic device that is configured to interact with the dentist.

B20.2. The method of paragraph B20.1, wherein the electronic device of paragraph B20.1 is a desktop computer.

B20.3. The method of paragraph B20.1, wherein the electronic device of paragraph B20.1 is a laptop computer.

B20.4. The method of paragraph B20.1, wherein the electronic device of paragraph B20.1 is a mobile electronic device.

B20.5. The method of paragraph B20.1, wherein the electronic device of paragraph B20.1 is a tablet computer.

B20.6. The method of paragraph B20.1, wherein the electronic device of paragraph B20.1 is a handheld electronic device.

B20.7. The method of paragraph B20.1, wherein the electronic device of paragraph B20.1 is a cellular/smart phone.

B21. The method of any of paragraphs B20-B20.7, wherein the dentist is a general practice dentist associated with the patient.

B21.1. The method of any of paragraphs B20-B20.7, wherein the dentist is an orthodontic assistant associated with the patient.

B21.2. The method of any of paragraphs B20-B20.7, wherein the dentist is an oral surgeon associated with the patient.

B21.3. The method of any of paragraphs B20-B20.7, wherein the dentist is an endodontic specialist associated with the patient.

B21.4. The method of any of paragraphs B20-B20.7, wherein the dentist is a periodontist associated with the patient.

B21.5. The method of any of paragraphs B20-B20.7, wherein the dentist is a prosthodontist associated with the patient.

B22. The method of any of paragraphs B20-B21.5, wherein the informational resource is a dentist-oriented informational resource that corresponds to a determined treatment instruction for a patient of the orthodontist, wherein the treatment instruction is selected by the orthodontist to be executed by the dentist.

B23. The method of any of paragraphs B20-B21.5, wherein the informational resource is the patient-oriented informational resource that corresponds to a determined treatment instruction for a patient of the orthodontist, wherein the treatment instruction is selected by the orthodontist to be executed by the patient.

B24. The method of any of paragraphs B20-B23, wherein the method further includes electronically providing the receipt information to the dentist.

INDUSTRIAL APPLICABILITY

The systems and methods disclosed herein are applicable to the medical field, including the orthodontic and dental care industries.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

The invention claimed is:

1. A method of electronically delivering an orthodontic treatment instruction to a patient of an orthodontist, the method comprising: determining the orthodontic treatment instruction for the patient to perform as a part of an orthodontic treatment; selecting a patient-oriented informational resource corresponding to the orthodontic treatment instruction; electronically delivering the patient-oriented informational resource to the patient; and receiving receipt information, wherein the receipt information is based on the patient- oriented informational resource being accessed by the patient; wherein the receipt information is received by the orthodontist regardless of a response from the patient, and wherein the receipt information changes state responsive to a patient- oriented digital media file corresponding to the patient-oriented informational resource being accessed by the patient; wherein the receipt information includes at least one of: data indicating whether the patient accessed the patient-oriented digital media file corresponding to the patient-oriented informational resource; and data indicating when the patient accessed the patient-oriented digital media file corresponding to the patient-oriented informational resource; responsive to receipt of the receipt information by the orthodontist, monitoring, by the orthodontist, patient compliance with the orthodontic treatment instruction provided by the patient-oriented informational resource; and adjusting, by the orthodontist, the patient's orthodontic treatment responsive to lack of compliance with the orthodontic treatment instruction provided by the patient-oriented informational resource to create an adjusted orthodontic treatment that compensates for the lack of compliance, and administering the adjusted orthodontic treatment to the patient by the orthodontist.

2. The method of claim 1, wherein the method further includes repeating the electronically delivering the patient-oriented informational resource to the patient if the receipt information indicates that the patient has not accessed the patient-oriented digital media file within a predetermined interval of time following the delivery of the patient-oriented informational resource to the patient.

3. The method of claim 1, wherein the electronically delivering the patient-oriented informational resource to the patient includes electronically transmitting the patient-oriented informational resource to a patient electronic device associated with the patient, wherein the patient electronic device is at least one of a desktop computer, a laptop computer, a tablet computer, a mobile electronic device, a handheld electronic device, a cellular phone, and a smart phone.

4. The method of claim 1, wherein the receipt information includes data indicating whether the patient has accessed the patient-oriented digital media file and data indicating when the patient accessed the patient-oriented digital media file.

5. The method of claim 1, wherein the monitoring includes receiving, by the orthodontist, a patient communication from the patient regarding the orthodontic treatment instruction corresponding to the patient-oriented informational resource.

6. The method of claim 5, wherein the patient communication includes a report of the patient executing the orthodontic treatment instruction corresponding to the patient-oriented informational resource.

7. The method of claim 1, wherein the patient-oriented informational resource is configured to permit the patient to access a patient-oriented digital media file.

8. The method of claim 1, wherein the patient-oriented digital media file is configured to communicate the orthodontic treatment instruction to the patient.

9. The method of claim 1, wherein the patient-oriented digital media file includes at least one of a digital video file, a digital text file, a digital image file, a digital audio file, a portable document format file, and a digital animation file.

10. The method of claim 1, wherein the orthodontist is at least one of an individual orthodontist, a group of orthodontists, an orthodontic practice, a team of orthodontists, an orthodontic technician, an orthodontic staff member, and an orthodontic assistant.

11. The method of claim 1, wherein the patient-oriented digital media file is selected from a plurality of preexisting patient-oriented digital media files.

12. The method of claim 1, wherein the patient-oriented informational resource includes at least one of a link to a web site, a code configured to be inputted at a web site, and an instruction for accessing the patient-oriented digital media file via an electronic interface.

13. The method of claim 1, wherein the method further includes notifying the orthodontist if the patient has not accessed the patient-oriented digital media file within a predetermined interval of time following the electronically delivering of the patient-oriented informational resource to the patient.

14. The method of claim 1, wherein the selecting the patient- oriented informational resource includes selecting from an orthodontist electronic device that is configured to interact with the orthodontist; wherein the orthodontist electronic device is at least one of a desktop computer, a laptop computer, a tablet computer, a mobile electronic device, a handheld electronic device, a cellular phone, and a smart phone; and wherein the electronically delivering the patient-oriented informational resource to the patient includes electronically delivering the patient-oriented informational resource to a patient electronic device associated with the patient, wherein the patient electronic device is at least one of a desktop computer, a laptop computer, a tablet computer, a mobile electronic device, a handheld electronic device, a cellular phone, and a smart phone.

15. The method of claim 14, wherein the method further includes electronically providing the patient-oriented informational resource to a caretaker of the patient; wherein the caretaker of the patient is at least one of a family member of the patient, a legal guardian of the patient, and an individual who is authorized to view the patient's orthodontic treatment records; wherein the electronically providing the patient-oriented informational resource to the caretaker includes electronically delivering the patient- oriented informational resource to a caretaker electronic device associated with the caretaker; and wherein the caretaker electronic device is at least one of a desktop computer, a laptop computer, a tablet computer, a mobile electronic device, a handheld electronic device, a cellular phone, and a smart phone; and wherein the caretaker electronic device is separate from the patient electronic device.

16. The method of claim 15, wherein the receipt information includes patient access data, and wherein the method includes the providing the patient-oriented informational resource to the caretaker of the patient via the caretaker electronic device if the patient access data indicates that the patient has not accessed the patient-oriented digital media file within a predetermined interval of time following the electronically delivering of the patient-oriented informational resource to the patient.

17. The method of claim 1, wherein the method further includes electronically providing a patient-oriented informational resource to a dentist; wherein the dentist is at least one of a general practice dentist associated with the patient, an orthodontic assistant associated with the patient, an oral surgeon associated with the patient, an endodontic specialist associated with the patient, a periodontist associated with the patient, and a prosthodontist associated with the patient; wherein the electronically providing the patient—oriented informational resource to the dentist includes electronically delivering the patient oriented informational resource to a dentist electronic device that is configured to interact with the dentist wherein the dentist electronic device is at least one of a desktop computer, a laptop computer, a tablet computer, a mobile electronic device, a handheld electronic device, a cellular phone, and a smart phone.

18. The method of claim 17, wherein the method further includes electronically providing the receipt information to the dentist.

19. The method of claim 17, wherein the electronically providing the patient-oriented informational resource to the dentist includes electronically providing a dentist- oriented patient-oriented informational resource to the dentist; wherein the dentist-oriented patient-oriented informational resource corresponds to at least one of a referral for dental treatment, patient information, patient dental information, and a determined dentist treatment instruction for the patient; and wherein the dentist treatment instruction is selected by the orthodontist to be executed by the dentist.

20. The method of claim 17, wherein the method further includes, responsive to an interaction between the patient and the dentist, electronically providing to the orthodontist a referral patient-oriented informational resource from the dentist, wherein the referral patient-oriented informational resource includes at least one of a referral for orthodontic treatment, patient information, and patient dental information.

21. The method of claim 1, wherein the method further includes electronically providing to the orthodontist a patient communication from the patient regarding the patient's orthodontic treatment.

22. The method of claim 21, wherein the patient communication includes an image of the patient's teeth.

23. The method of claim 22, wherein the method further includes electronically transmitting the image of the patient's teeth to at least one dental care provider other than the orthodontist, and wherein the method still further includes electronically transmitting a medical opinion from the at least one dental care provider to the orthodontist, wherein the medical opinion is based, at least in part, on the image of the patient's teeth.

24. The method of claim 22, wherein the method further includes, responsive to the orthodontist receiving the image of the patient's teeth, determining, by the orthodontist, at least one of an orthodontic treatment and an orthodontic treatment instruction for the patient.

* * * * *